(12) United States Patent
Makower et al.

(10) Patent No.: US 11,089,991 B2
(45) Date of Patent: Aug. 17, 2021

(54) SYSTEMS, DEVICES AND METHODS FOR ASSESSING MILK VOLUME EXPRESSED FROM A BREAST

(71) Applicant: EXPLORAMED NC7, INC., Mountain View, CA (US)

(72) Inventors: Joshua Makower, Los Altos Hills, CA (US); John Y Chang, Los Altos, CA (US); Theodore M Bender, San Anselmo, CA (US); Brendan M Donohoe, Fairfax, CA (US)

(73) Assignee: Willow Innovations, Inc., Mountain View, CA (US)

(*) Notice: Subject to any disclaimer, the term of this patent is extended or adjusted under 35 U.S.C. 154(b) by 756 days.

(21) Appl. No.: 15/448,716

(22) Filed: Mar. 3, 2017

(65) Prior Publication Data

US 2017/0172485 A1  Jun. 22, 2017

Related U.S. Application Data

(63) Continuation of application No. PCT/US2015/050340, filed on Sep. 16, 2015.
(Continued)

(51) Int. Cl.
*A61B 5/00* (2006.01)
*A61M 1/06* (2006.01)

(52) U.S. Cl.
CPC .............. *A61B 5/4312* (2013.01); *A61M 1/06* (2013.01); *A61B 5/0022* (2013.01); *A61B 2562/0261* (2013.01); *A61M 2205/3569* (2013.01); *A61M 2205/3576* (2013.01); *A61M 2205/3584* (2013.01); *A61M 2205/60* (2013.01); *A61M 2210/1007* (2013.01)

(58) Field of Classification Search
CPC ........ A61M 1/06; A61M 1/062; A61M 1/064; A61M 2205/3331; A61M 2205/3334; A61M 2205/3569; A61M 2205/3584; A61M 2210/1007; A61M 2205/3576; A61B 5/4288; A61B 5/4312; A61B 6/502; A61B 5/1073; A61B 2018/00333
USPC .... 600/300, 587, 547, 476; 604/74, 75, 326, 604/514
See application file for complete search history.

(56) References Cited

U.S. PATENT DOCUMENTS 4,219,029 A * 8/1980 Grossman ............ A61B 5/1073
  33/2 R
4,263,912 A 4/1981 Adams
(Continued)

FOREIGN PATENT DOCUMENTS

CN 2628060 Y 7/2004
CN 201353322 12/2009
(Continued)

OTHER PUBLICATIONS

Chiu et al., Development of a piezoelectric polyvinylidene fluoride (PVDF) polymer based sensor patch for simultaneous heartbeat and respiration monitoring, Sensors and Actuators A: Physical, vol. 189, Jan. 15, 2013, pp. 328-334.
(Continued)

*Primary Examiner* — May A Abouelela

(57) ABSTRACT

Systems and methods for assessing milk volume changes within a breast are described. Also described are systems and methods for assessing volume changes in the stomach of an infant.

14 Claims, 10 Drawing Sheets

Related U.S. Application Data

(60) Provisional application No. 62/062,232, filed on Oct. 10, 2014, provisional application No. 62/050,902, filed on Sep. 16, 2014.

(56) References Cited

U.S. PATENT DOCUMENTS

| | | | |
|---|---|---|---|
| 5,542,921 A | 8/1996 | Meyers et al. | |
| 5,634,468 A | 6/1997 | Platt et al. | |
| 5,827,191 A | 10/1998 | Rosenfeld | |
| 5,902,267 A | 5/1999 | Medo | |
| 6,033,367 A | 3/2000 | Goldfield | |
| 6,045,529 A | 4/2000 | Nuesch | |
| 6,122,544 A * | 9/2000 | Organ | A61B 5/0531 600/547 |
| 6,264,049 B1 | 7/2001 | Shteynberg | |
| 6,273,868 B1 | 8/2001 | Nordvik | |
| 6,287,252 B1 | 9/2001 | Lugo | |
| 6,328,082 B1 | 12/2001 | Lafond | |
| 6,379,327 B2 | 4/2002 | Lundy | |
| 6,440,100 B1 | 8/2002 | Prentiss | |
| 6,547,756 B1 | 4/2003 | Greter et al. | |
| 6,712,785 B2 | 3/2004 | Morton et al. | |
| 6,981,988 B1 * | 1/2006 | Kinsley | A61F 2/12 33/2 R |
| 7,201,735 B2 | 4/2007 | Atkin et al. | |
| 7,223,255 B2 | 5/2007 | Myers et al. | |
| 7,559,915 B2 * | 7/2009 | Dao | A61M 1/06 450/36 |
| D604,503 S | 11/2009 | Patadia | |
| 7,621,797 B1 | 11/2009 | Hershkovich | |
| 7,824,363 B2 | 11/2010 | Myers | |
| 7,835,230 B1 | 11/2010 | Chang | |
| 7,988,661 B2 | 8/2011 | Silver et al. | |
| 8,057,425 B1 | 11/2011 | Myers et al. | |
| 8,070,715 B2 | 12/2011 | Quackenbush et al. | |
| 8,070,716 B2 | 12/2011 | Sutrina et al. | |
| 8,114,030 B2 * | 2/2012 | Ales | A61B 5/4312 600/584 |
| 8,118,772 B2 | 2/2012 | Dao | |
| 8,262,606 B2 | 9/2012 | Greter et al. | |
| 8,282,596 B2 | 10/2012 | Greter et al. | |
| 8,353,865 B2 | 1/2013 | Thilwind et al. | |
| 8,376,986 B2 | 2/2013 | Van Schijndel et al. | |
| 8,597,234 B2 | 12/2013 | Larsson | |
| 8,671,701 B2 | 3/2014 | McKendry | |
| 8,684,961 B2 | 4/2014 | Gottenbos et al. | |
| 8,801,495 B1 | 8/2014 | Guindon | |
| 8,801,658 B2 * | 8/2014 | Harari | A61B 5/1075 604/74 |
| 8,979,819 B2 | 3/2015 | Sherman | |
| 8,992,445 B2 * | 3/2015 | Blondheim | A61B 5/11 600/587 |
| 9,050,404 B2 | 6/2015 | Silver et al. | |
| 9,162,016 B2 | 10/2015 | Geddes | |
| 9,173,587 B2 | 11/2015 | Van Schijndel et al. | |
| 9,199,017 B2 | 12/2015 | Greter | |
| 9,211,366 B1 * | 12/2015 | Gutwein | A61B 5/4288 |
| 9,278,167 B2 | 3/2016 | Aalders et al. | |
| 2003/0073951 A1 * | 4/2003 | Morton | A61B 5/6834 604/73 |
| 2003/0191433 A1 | 10/2003 | Prentiss | |
| 2005/0059928 A1 * | 3/2005 | Larsson | A61B 5/053 604/74 |
| 2005/0234370 A1 | 10/2005 | Beal et al. | |
| 2006/0106334 A1 | 5/2006 | Jordan et al. | |
| 2008/0039741 A1 * | 2/2008 | Shemesh | A61B 5/411 600/584 |
| 2008/0077042 A1 * | 3/2008 | Feldkamp | A61B 5/103 600/547 |
| 2008/0097169 A1 * | 4/2008 | Long | A61B 5/103 600/301 |
| 2008/0262420 A1 * | 10/2008 | Dao | A61M 1/06 604/74 |
| 2009/0287119 A1 * | 11/2009 | Chapman | A61B 5/4312 600/587 |
| 2009/0326396 A1 | 12/2009 | Aliverti et al. | |
| 2010/0217148 A1 * | 8/2010 | Binder | A61B 5/0536 600/547 |
| 2010/0292604 A1 * | 11/2010 | Kapon | A61B 5/0535 600/547 |
| 2011/0034869 A1 | 2/2011 | Greter | |
| 2011/0036801 A1 | 2/2011 | Martijn | |
| 2011/0071466 A1 * | 3/2011 | Silver | A61M 1/0072 604/74 |
| 2011/0098549 A1 | 4/2011 | Bar Hayim et al. | |
| 2011/0245763 A1 | 10/2011 | Myers | |
| 2011/0251552 A1 | 10/2011 | Brittner | |
| 2012/0004603 A1 * | 1/2012 | Harari | A61B 5/1075 604/74 |
| 2012/0197187 A1 | 8/2012 | LaFave | |
| 2012/0277636 A1 | 11/2012 | Blondheim | |
| 2012/0277728 A1 | 11/2012 | Weber et al. | |
| 2013/0023821 A1 | 1/2013 | Khalil et al. | |
| 2013/0123688 A1 | 5/2013 | Bosman et al. | |
| 2013/0131588 A1 | 5/2013 | Silver et al. | |
| 2013/0178793 A1 | 7/2013 | Matias | |
| 2013/0218045 A1 | 8/2013 | Ironstone | |
| 2013/0338528 A1 | 12/2013 | Kapon et al. | |
| 2014/0008317 A1 * | 1/2014 | Yang | A61J 13/00 215/11.1 |
| 2014/0066734 A1 | 3/2014 | Zdeblick | |
| 2014/0128806 A1 * | 5/2014 | Schlienger | A61M 1/06 604/74 |
| 2014/0142501 A1 | 5/2014 | Clark | |
| 2014/0242213 A1 | 8/2014 | McCarty | |
| 2014/0263611 A1 * | 9/2014 | Bauer | A61M 1/06 235/375 |
| 2014/0288466 A1 | 9/2014 | Alvarez | |
| 2014/0311239 A1 | 10/2014 | Marjanovic | |
| 2014/0378895 A1 | 12/2014 | Barack | |
| 2014/0378946 A1 | 12/2014 | Thompson | |
| 2015/0065994 A1 * | 3/2015 | Fridman | A61M 1/06 604/514 |
| 2015/0065996 A1 | 3/2015 | Bartlett, II | |
| 2015/0112298 A1 | 4/2015 | Pirzada | |
| 2015/0150761 A1 | 6/2015 | Lanternari | |
| 2017/0136160 A1 | 5/2017 | Barral et al. | |
| 2019/0046103 A1 * | 2/2019 | Henderson | A61B 5/4288 |
| 2019/0209747 A1 * | 7/2019 | Analytis | A61M 1/06 |

FOREIGN PATENT DOCUMENTS

| | | |
|---|---|---|
| CN | 102149415 | 8/2011 |
| CN | 20223080 | 5/2012 |
| DE | 10 2008 052406 A1 | 2/2010 |
| DE | 102008052406 | 2/2010 |
| EP | 2456482 B1 | 11/2016 |
| GB | 2342446 A | 4/2000 |
| GB | 2 444 145 A | 5/2008 |
| GB | 2444145 | 5/2008 |
| KR | 20110073002 | 6/2011 |
| WO | WO2000041745 | 7/2000 |
| WO | WO2001054488 | 8/2001 |
| WO | WO2003028616 | 4/2003 |
| WO | WO2011010255 | 1/2011 |
| WO | WO2011144984 A | 11/2011 |
| WO | WO2013088310 | 6/2013 |
| WO | WO2013166462 | 11/2013 |
| WO | WO2013184004 | 12/2013 |
| WO | WO2014/087343 | 6/2014 |
| WO | WO 2014087343 A1 | 6/2014 |
| WO | WO2015120321 | 8/2015 |

OTHER PUBLICATIONS

Double Electric Breast Pump/Dr. Brown's,http://www.drbrownsbaby.com/breastfeeding-product/breast-pumps/double-electric, May 15, 2014.

(56) References Cited

OTHER PUBLICATIONS

Sadleir, Rosalind; Shape capture, analysis and registration, Australian Journal of Intelligent Information Processing Systems, 2000, pp. 12-17, vol. 6, No. 1, Australia.
Arthur, Peter G. et al., Measuring Short-term Rates of Milk Synthesis in Breast-Feeding Mothers, Experimental Physiology, 1989, pp. 419-428, Great Britain.

* cited by examiner

SYSTEMS, DEVICES AND METHODS FOR ASSESSING MILK VOLUME EXPRESSED FROM A BREAST

FIELD OF THE DISCLOSURE

The present disclosure generally relates to systems and methods for assessing milk volume in the breast, milk volume expressed from the breast and milk volume consumed by an infant.

BACKGROUND OF THE DISCLOSURE

The American Academy of Pediatrics (AAP), American Academy of Family Physicians (AAFP), Center for Disease Control (CDC), U.S. Department of Health and Human Services (USDHHS), American Public Health Association (APHA) and International Lactation Consultant Association (ILCA) all recommend at least one year of exclusive breast-feeding of an infant from birth. It is estimated that if ninety percent of U.S. families followed this guideline, this would result in nine hundred infant deaths prevented per year and thirteen billion dollars in costs averted.

Measuring the amount of breast milk suckled by a baby is important to ensure that the baby is being properly fed. Knowing the amount of breast milk ingested by a baby can help to evaluate the baby's nutritional status, the need for breastfeeding guidance, or the use of milk substitutes. This information can be useful to the feeding mother, as well as her attending health care professionals.

Methods and systems for determining milk volume expressed during breastfeeding have been previously proposed. One method involves weighing the baby before and after feeding. The difference in weight between the before and after measurements can be correlated to an estimate of the amount of milk that the baby has ingested. The accuracy of this method can vary depending upon the accuracy of the scales used. Additionally, it is not always possible for the nursing mother or someone else to weigh the baby before and after each feeding, and even during feedings where this is possible, it is not convenient.

U.S. Pat. No. 5,827,191 which is incorporated herein, in its entirety, by reference thereto, discloses a method of monitoring the volume of milk during breastfeeding by applying a porous elastic nipple-shaped cover over the nipple area of a women's breast, which is present during the breastfeeding. A micro-measurement sensor is located in a space between the nipple and the elastic cover to measure the volume of the milk flowing therethrough. Data from the sensor is gathered and then processed to indicate total milk volume intake by the baby. This method may negatively affect the breastfeeding session, as a mechanically rotating device is placed in the milk flow path, which will likely at least partially impede the flow of milk from the breast to the baby, which could result in less milk being delivered to the baby and/or longer breastfeeding sessions required to deliver a volume of milk that would ordinarily be delivered in less time if the rotary mechanism were not present. Additionally, since components are exposed to the milk, they will need to be cleaned frequently, which is not convenient.

U.S. Patent Application Publication No. 2005/0059928 which is hereby incorporated herein, in its entirety, by reference thereto, a breast shield that includes one or more sensors configured to sense changes in the breast. The sensor(s) can be optical, acoustical, thermal, or electrical and can be used for ultrasound, detection and measurement of electrical activity which records, for example, resistance and impedance between two spaced areas of the breast, and so on. Electrodes are placed on the breast skin for measuring electric signals, optical sensors for detecting and/or measuring, for example, light absorption or reflection, and acoustic sensors for detecting and/or measuring ultrasound. The sensor(s) can be used to detect a change in conductance of the breast during milk pumping using a breast pump, so that the pump can be programmed to be responsive to the change in signal. A breast shield incorporating optical sensing devices can be used to facilitate sensing of light reflected from the breast to convey the light to an optical spectrum analyzing instrument. Changes in the breast detectable by changes in the reflected light may be used in studying milk production and expression and may be used as a control signal in controlling a breast pump.

WO 01/54488 A, which is hereby incorporated herein, in its entirety, by reference thereto, discloses a feeding cap that is configured to be mounted over the nipple of the nursing mother prior to a breastfeeding session. The feeding cap contains a flow meter that measures the amount of milk passing through an outlet in the feeding cap.

There is a need for convenient and accurate devices and methods for measuring the amount of milk expressed from a breast.

There is a need for devices and methods that can measure the amount of milk expressed from a breast, without the need to contact the milk expressed from the breast.

SUMMARY OF THE DISCLOSURE

According to one aspect of the present disclosure, a method for assessing milk volume changes within a breast includes: attaching a device to the breast, the device including at least one expansile portion and a sensor configured to sense an amount of expansion or contraction of skin of the breast to which the device is attached; sensing an amount of contraction or expansion of the skin to which the device is attached; and calculating a volume change of the breast based on the amount of contraction or expansion sensed.

In at least one embodiment, the method further includes calculating an amount of milk produced or expressed based on the volume change of the breast having been calculated.

In at least one embodiment, the method further includes transmitting signals representative of the amount of contraction or expansion sensed to an external computing device; wherein the calculating a volume change is performed by the external computing device.

In at least one embodiment, the method further includes uploading at least one of the signals and the volume change having been calculated to a network.

In at least one embodiment, the network is the Internet.

In at least one embodiment, at least one of the signals and the volume change are uploaded to a cloud-based server.

In at least one embodiment, the volume change calculation is performed by the device.

In at least one embodiment, the method further includes automatically uploading at least one of signals resulting from the sensing an amount of contraction or expansion of the skin and the volume change having been calculated to a network.

In at least one embodiment, the method further includes: sensing a change in pressure between the breast and a bra supporting the breast; wherein the calculating a volume change of the breast is based on the amount of contraction or expansion sensed and the change in pressure sensed.

In at least one embodiment, the method further includes stretching the device prior to the attaching, to enhance a capability of the device to sense contraction of the breast.

In another aspect of the present disclosure, a method of monitoring a breast includes: applying at least one indicator to the skin of the breast; sensing an amount of contraction or expansion of the skin in a location at which the at least one indicator is applied; and calculating at least one of a volume of the breast and volume change of the breast based on the amount of contraction or expansion sensed.

In at least one embodiment, the calculating is performed by at least one processor of a computer, the method further comprising outputting the at least one of breast volume and change in breast volume having been calculated, for use by a user.

In at least one embodiment, the method further includes calculating at least one of milk volume and change in milk volume of the breast.

In at least one embodiment, the calculating is performed by at least one processor of a computer, the method further comprising outputting the at least one of milk volume and change in milk volume having been calculated, for use by a user.

In at least one embodiment, the method further includes repeating the sensing of change in pressure, breast volume change calculation and calculation of at least one of milk volume change and change in milk volume of the breast at multiple different times; and recording results of the calculations.

In at least one embodiment, the method further includes plotting or tabulating the calculations iteratively performed; and outputting a plot or table resulting from the plotting or tabulating for use by a user.

In at least one embodiment, the application of at least one indicator to the skin of the breast includes attaching a device to the skin, the device comprising at least one non-expansile portion and an expansile portion.

In at least one embodiment, the sensing is carried out by the device, the method further including transmitting signals representative of an amount of expansion or contraction of the skin sensed by the device to an external computer, wherein the calculating is performed by the external computer.

In at least one embodiment, the sensing and the calculating are carried out by the device.

In at least one embodiment, the method further includes transmitting signals representative of at least one of an amount of expansion or contraction of the skin sensed by the device and results of the calculating to an external computer.

In at least one embodiment, the device is self-powered and the sensing and transmitting are actively performed.

In at least one embodiment, the device is a passive device, powered by the external computer to perform the transmitting.

In at least one embodiment, the transmitting comprises automatically uploading the signals to an external computer.

In at least one embodiment, the external computer comprises a smartphone.

In at least one embodiment, the external computer comprises a tablet computer.

In at least one embodiment, the external computer comprises a cloud-based server.

In at least one embodiment, the sensing comprises measuring a distance between a fixed point on the non-expansile portion and a predetermined point on the expansile portion.

In at least one embodiment, the sensing comprises making a digital image of the device, uploading the digital image to a program on the external computer configured to perform the measuring; and executing the program to perform the measuring.

In at least one embodiment, the calculating is performed by execution of the program by a processor of the external computer.

In at least one embodiment, the external computer comprises a camera, and the making a digital image comprises taking a photo using the camera.

In at least one embodiment, the sensing comprises scanning the device, uploading data resulting from the scanning to a program on the external computer configured to perform the measuring; and executing the program to perform the measuring.

In at least one embodiment, the method further includes: taking baseline measurements of the breast prior to the sensing; and including the baseline measurements as inputs for the calculating at least one of a volume of the breast and volume change of the breast based on the amount of contraction or expansion sensed.

In at least one embodiment, the baseline measurements comprise a circumferential measurement of the breast and an anterior-posterior (AP) measurement of the breast.

In at least one embodiment, the method further includes: calculating a baseline volume of the breast based upon a breast cup size; and including the baseline volume for calculating at least one of a volume of the breast and volume change of the breast based on the amount of contraction or expansion sensed.

In at least one embodiment, the sensing includes: sensing when a user indicates that the breast is in a first state; and sensing when the user indicates that the breast is in a second state; wherein the calculating comprises calculating a benchmark first state volume using sensing results when the user indicates that the breast is in the first state; and calculating a benchmark second state volume using sensing results when the user indicates that the breast is in the second state.

In at least one embodiment, the first state is full and the second state is empty.

In at least one embodiment, the applying at least one indicator to the skin of the breast includes: attaching a device to the skin, the device comprising an expansile portion; and wherein the sensing an amount of contraction or expansion of the skin in a location at which the at least one indicator is applied comprises measuring a distance between a predetermined location on the expansile portion and a relatively fixed point on the breast.

In at least one embodiment, the relatively fixed point is on the nipple of the breast.

In at least one embodiment, the applying at least one indicator to the skin of the breast comprises marking the breast with at least one mark at a location that is predetermined distance from another predetermined location on the breast.

In at least one embodiment, the another predetermined location is on the nipple of the breast.

In at least one embodiment, the at least one indicator comprises two marks applied at predetermined locations relative to one another.

In at least one embodiment, the sensing and calculating are performed before and after breast feeding a baby, the method further including: applying a breast pump to the breast and pumping milk from the breast; the breast pump sensing a volume of milk expressed during the pumping milk; and calculating a volume of milk expressed during the pumping milk.

In at least one embodiment, the method further includes combining the calculations of at least one of milk volume and milk volume change of the breast with calculation of milk volume expressed during pumping milk to track overall milk production and expression during breast feeding and breast pumping over time.

In at least one embodiment, the method further includes: applying a breast pump to the breast and pumping milk from the breast; wherein the sensing and calculating are performed immediately before and after the pumping; and tracking calculations resulting from the sensing and calculating before and after breast feeding, as well as breast pumping, to track overall milk production and expression.

In another aspect of the present disclosure, a system for monitoring changes in a body part is provided, including: at least one indicator configured and dimensioned to be applied to skin overlying the body part; an external computer configured to, together with the at least one indicator: sense an amount of contraction or expansion of the skin in a location at which the at least one indicator is applied; and calculate at least one of a volume of the body part and volume change of the body part.

In one approach, one or more sensors can be provided and affixed to skin to detect one or more of temperature, heart-rate, respiration, or motion. Such variables can be useful to manage other health parameters.

In at least one embodiment, the at least one indicator comprises a device configured to be attached to the skin, the device including: a relatively non-expansile portion; and an expansile portion configured to expand and contract with expansion of the skin relative to the relatively non-expansile portion.

In at least one embodiment, the system further includes a sensor mounted on the device, the sensor configured to sense expansion and contraction of the expansile portion.

In at least one embodiment, the system further includes: a circuit electrically connected to the sensor; and an antenna electrically connected to the circuit; the circuit being configured to receive input from the sensor and send signals representative of the expansion or contraction sensed to the external computer via the antenna.

In at least one embodiment, the device further includes a battery electrically connected to the circuit to power the device.

In at least one embodiment, the device further includes electronic memory configured to store data received from the sensor by the circuit.

In at least one embodiment, the sensor is mounted on a patch that is removably attached to at least one of the expansile and relatively non-expansile portions, wherein the expansile and relatively non-expansile portions are disposable and the patch is reusable.

In at least one embodiment, at least one of the sensor, circuit and antenna is mounted on a patch that is removably attached to at least one of the expansile and relatively non-expansile portions, wherein the expansile and relatively non-expansile portions are disposable and the patch is reusable.

In at least one embodiment, at least one of the sensor, circuit, antenna and battery is mounted on a patch that is removably attached to at least one of the expansile and relatively non-expansile portions, wherein the expansile and relatively non-expansile portions are disposable and the patch is reusable.

In at least one embodiment, at least one of the sensor, circuit, antenna, battery and memory is mounted on a patch that is removably attached to at least one of the expansile and relatively non-expansile portions, wherein the expansile and relatively non-expansile portions are disposable and the patch is reusable.

In at least one embodiment, the device includes a passive device that is actuated and powered by the external computer.

In at least one embodiment, the external computer includes a digital camera, and the amount of contraction or expansion of the skin is sensed by taking a digital photograph of the device and inputting the digital data to a program executable by at least one processor of the external computer; wherein the program is executable by the at least one processor to: measure a distance between a predetermined location on the relatively non-expansile portion and a predetermined location on the expansile portion; and perform the calculation of at least one of a volume of the body part and volume change of the body part.

In at least one embodiment, the program is further configured to receive baseline data regarding a volume of the body part prior to sensing, the baseline data being used in conjunction with data from the distance measured to perform the calculation of at least one of a volume of the body part and volume change of the body part.

In at least one embodiment, data detected from the system can be integrated with a pump system that also reports milk production via phone or the cloud or computer so that a total milk produced/milk consumed estimate can be calculated. The system can also be configured to be detected directly by the pump, or indirectly via a phone, so that the measurement detected could be calibrated.

In at least one embodiment, the body part is a breast.

In at least one embodiment, the body part is a baby's stomach.

In at least one embodiment, the external computer is further configured to calculate at least one of a volume of milk in the breast change of volume of milk in the breast.

In at least one embodiment, the body part is a breast, the system further including: a breast pump; wherein the external computer is configured to, together with the at least one indicator: sense an amount of contraction or expansion of the skin of the breast during the breast pumping, in a location at which the at least one indicator is applied; and calculate at least one of a volume of the breast and volume change of the breast.

In at least one embodiment, the body part is a breast, the system further including: a breast pump; wherein the breast pump is configured to measure at least one of flow of milk and milk volume expressed during a breast pumping session using the breast pump; and wherein the external computer is configured to receive data representative of measurement of the at least one of flow of milk and milk volume and incorporate the data representative of measurement of the at least one of flow of milk and milk volume with calculations of the at least one of a volume of the breast and volume change of the breast to calculate and track milk volume production over multiple breast feeding and breast pumping sessions.

In another aspect of the present disclosure, a method of monitoring a breast includes: applying at least one sensor to the skin of the breast; sensing an amount of contraction or expansion of the skin in a location at which the at least one sensor is applied; and calculating at least one of a volume of the breast and volume change of the breast based on the amount of contraction or expansion sensed.

In at least one embodiment, the sensing includes sensing the amount of contraction or expansion by measuring a change in capacitance at the at least one sensor.

In at least one embodiment, the sensing includes sensing the amount of contraction or expansion by measuring an impedance change at the at least one sensor.

In at least one embodiment, the sensing includes sensing the amount of contraction or expansion by sensing acoustic changes of acoustic waves delivered into the breast.

In at least one embodiment, the sensing includes sensing the amount of contraction or expansion by sensing a change in pressure applied by the breast against a supporting bra.

In at least one embodiment, the sensing includes sensing the amount of contraction or expansion by measuring an electrical resistance change in the breast.

In at least one embodiment, the sensing includes sensing the amount of contraction or expansion by measuring a density change of the breast.

These and other advantages and features of the disclosure will become apparent to those persons skilled in the art upon reading the details of the systems and methods as more fully described below.

DETAILED DESCRIPTION OF THE DISCLOSURE

Figure 1:
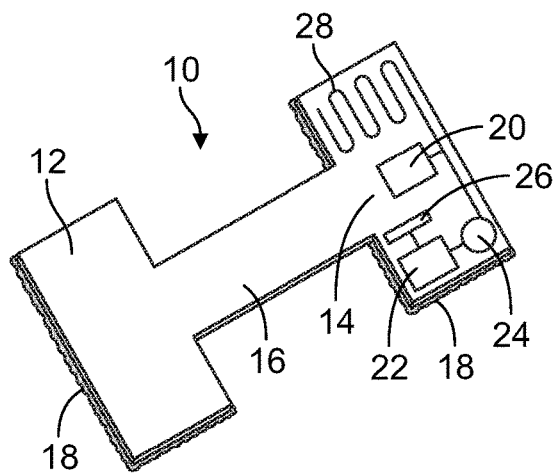
FIG. 1 is a perspective, schematic illustration of a device configured to be adhered to the skin of a subject to detect expansion and contraction of the skin, according to an embodiment of the present disclosure.

Before the present devices, systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a pattern" includes a plurality of such patterns and reference to "the algorithm" includes reference to one or more algorithms and equivalents thereof known to those skilled in the art, and so forth.

The publications discussed herein are provided solely for their disclosure prior to the filing date of the present application. The dates of publication provided may be different from the actual publication dates which may need to be independently confirmed.

In one aspect of the present disclosure, a non-invasive method and device are provided for assessing milk volume changes within a human breast. This includes means for detecting expansion or contraction of the breast skin tissue and correlating those changes to a predetermined baseline to render a calculation as to the change of volume within the breast. The system includes a device applied directly to the skin and another device which has been pre-configured with a means for detecting the skin device and also rendering a calculation based upon internal algorithms and also possibly initial baseline measurements on the breast itself. Once calculated, a volume and volume change is presented to the user.

In addition to assessing changes in distance or strain on breast tissue, breast firmness can be sensed and quantified, and correlated to milk production and expression. Baseline firmness, and other stages of breast conditions, can be identified and included in facilitating correlation to milk production and expression. Hardness tests as well as firmness or tautness assessments can be conducted to further or specifically quantify the firmness of a breast. In one or more approaches, one or more sensors also can be provided and affixed to skin to detect one or more of temperature, heartrate, respiration, or motion. Such variables can be useful to manage other health parameters.

In at least one embodiment, the device applied to the skin comprises a pattern on a very flexible and expansile surface capable of being adhered closely to the skin surface. The pattern having at least one region that cannot change in a dimension and another region that can change in at least one or more directions.

An app developed for a smartphone or other electronic device with a camera can be used to sense the image of the pattern and, as a result, correlate the changes in the pattern using any predetermined baseline measurements, and render a volume change/amount that correlates to the changes in the pattern.

In another embodiment, a device configured to be adhered to the skin comprises at least one elastic element capable of being mechanically altered via the stretch or compression of a region of the skin. In a coupling relationship to this elastic element, an electronic element such as a resistor, magnet or strain gage is coupled such that changes in the tension or compression of the elastic element are translated into a change in the electronic element. The electronic element is further coupled to an antenna capable of receiving power, and the same or another antenna capable of transmitting. Upon activation by a second device, the skin device is activated and sends a signal back corresponding to the state of stretch of the skin device. The signal is interpreted by the second device and correlated using an algorithm to output the measured volume change of the breast.

In another embodiment, the device adhered to the skin can include a power source and a circuit to handshake with the second device, activate when needed, and to send the tension/compression electronic information to the second device.

In another embodiment, the device adhered to the skin includes memory configured to store multiple data points of tension/compression information which is downloadable at any time by the second device, without requiring interrogation at specific intervals in the feeding cycle to provide useful information.

In another embodiment, the second device combines milk volume and time data obtained during breast feedings with milk volume and time data obtained from pumping milk with a breast pump system, to track total volumes of milk production over any specified time period.

Daly et al., "The Determination of Short-Term Breast Volume Changes and the Rate of Synthesis of Human Milk Using Computerized Breast Measurement", *Experimental Physiology* 91992) 79-87, which is hereby incorporated herein, in its entirety by reference thereto, demonstrated the relationship between breast volume changes and the rate of milk production. Therefore it is possible to measure changes in breast size to calculate an estimate of milk volume contained within the breast. Also, by measuring changes in breast volume as it contracts, a calculation of an estimate of milk volume expressed can be made. The following embodiments physically measure changes in the breast size when expanding or contracting. Alternatively, such breast size changes can be monitored by impedance, electrical resistance or acoustical measurement.

FIG. 1 is a perspective, schematic illustration of a device 10 configured to be adhered to the skin of a subject to detect expansion and contraction of the skin, according to an embodiment of the present disclosure. Although the preferred application of all the embodiments described herein is to the skin of the breast of a nursing mother, it is noted that all embodiments herein can be applied to any region of the skin where it is desired to measure changes (expansion and contraction) of the skin. Device 10 includes a distal mount portion 12, a proximal mount portion 14 and a flexible intermediate portion 16 that bridges the proximal 14 and distal 12 mount portions. The proximal mount portion has components mounted to it that measure changes in the skin that the device 10 is adhered to. The back surfaces of the distal and proximal mount portions 10, 12 have an adhesive 18 applied thereto so that the device 10 can be adhered to the skin, while the intermediate (bridge) portion 16 does not have any adhesive applied thereto, so that it can more freely expand and contract. There are various ways that the device 10 can be configured. In one preferred embodiment, an elastically expandable material (silicone, or any number of elastomers) can be used for all portions 12, 14 and 16, in order to render manufacturing easier and relatively less costly. Attached to or embedded within the portions 10 and 12 can be a reinforcing structure (e.g., a weave or non-expandable plastic or fabric), which renders the portions 10, 12 resistant to deformation. Additionally or alternatively to providing a reinforcing structure, the adhesive by which the portions 10, 12 are attached to the skin may provide or supplement the function of providing resistance to deformation. Alternatively to making all portions 12, 14, 16 of the same material, composite materials can be chosen so that the composite material provided for portions 12, 14 could include non-elastomeric material encased by or otherwise attached to elastomeric material, which may be the same as, or different from the elastic material used to form portion 16. Elastomeric materials may include, but are not limited to, one or more of silicones, polyurethanes, polyether block amides (PEBAX), polyethylene terephthalates (PET), polyethylenes, high density polyethylenes (HDPE), low density polyethylenes (LDPE), polyamides and/or other biocompatible thermoplastic elastomers. Materials that can be woven as reinforcing fabrics include, but are not limited to, one or more of: polytetrafluoroethylenes (PTFE), polyesters, polypropylenes, polyethylenes, para-aramid synthetic fibers and/or other biocompatible polymers used for making woven fabric. Non-expandable, or non-elastomeric materials that may be used include, but are not limited to, at least one of: acrylonitrile butadiene styrene (ABS) plastics, polyester fiberglasses, high density polyethylenes (HDPE), high impact polystyrenes (HIPS), nylon, polybutylene terephthalates (PBT), polyethylene terephthalates (PET), polycarbonates and/or other biocompatible, thermosetting polymers or none-expandable, non-elastomeric materials. Woven fabrics used may have either elastomeric or rigid properties depending on how they are configured and could therefore be used in portions 12,14 or portion 16, depending upon configuration for elastomeric properties or rigidity properties. Adhesives that may be used to adhere the portions 12, 14 to the skin include, but are not limited to, at least one of: pressure sensitive adhesives of the type used in ostomy applications, containing various rubber-like organic molecules such as polybutadiene and polyisobutylene, polyacrylate pressure sensitive adhesives, silicone adhesives, soft skin adhesives (Dow Corning®), skin friendly adhesives (Scapa Healthcare, Windsor, Conn.), removable adhesives (an adhesive designed to stick to a substrate without edge lifting that can be removed without damage to either the label or the substrate, such as available from Avery Dennison), and/or any other adhesive successfully used for temporary adherence to the skin.

The distal and proximal mount portions 12, 14 are adhered to the skin at locations that initially place the bridge portion 16 in an unbiased stated (neither stretched nor compressed). A sensor 20, such as an electric resistor, strain gauge, magnet or the like is provided on proximal mount 14 and is configured so that compression and expansion of the bridge portion 16 applies strain/forces to the sensor 20, which measures the amount of expansion or compression according to methods well understood in the strain measurement arts. In the embodiment shown in FIG. 1, a circuit 22 is provided on proximal mount that is powered by battery 24 and can be configured to process the output of the sensor 20, and store the processed signals in memory 26. Additionally, an antenna 28 is electrically connected to the circuit 22, which can be used to transmit the data stored in memory 26 to an external device such as a smartphone, tablet, or other computer, and/or to upload the data to a network, such as a cloud-based server or the like. In at least one embodiment, data detected from the system can be integrated with a pump system that also reports milk production via phone or the cloud or computer so that a total milk produced/milk consumed estimate can be calculated. The system can also be configured to be detected directly by the pump, or indirectly via a phone, so that the measurement detected could be calibrated.

Figure 2:
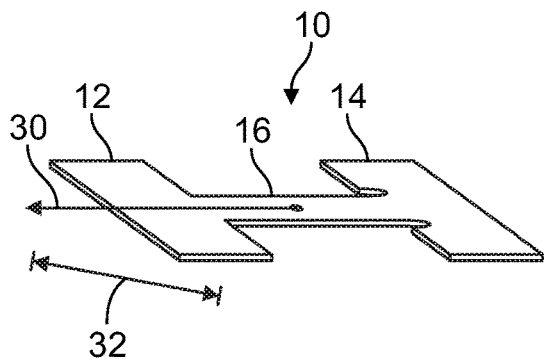
FIG. 2 is another schematic illustration of the device of FIG. 1.

Once adhered to the skin as described, expansion or contraction of the skin increases or decreases force in the bridge portion 16 as it stretches or contracts along with the movements of the skin. Referring to FIG. 2, as force 30 is applied to the device (expansion force, as illustrated in FIG. 2), the length of the bridge portion 16 changes with the expansion or contraction of the skin. The distance 32 by which the relative positions of the distal and proximal mounts 12, 14 change, which is also the amount of stretching or contraction of the bridge portion 16, is sensed by the sensor 20. When device 10 is adhered to the skin of the breast, the signal from sensor 20 can be correlated to a change in breast volume.

Figure 3:
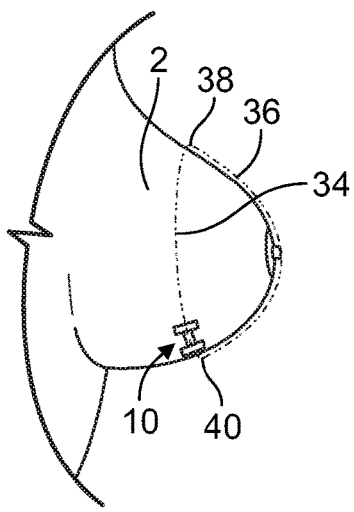
FIG. 3 illustrates the device of having been adhered to a breast, in accordance with an embodiment of the present disclosure.

In embodiments where baseline measurement are taken, the breast can be measured at (or just prior to) the time that the device 10 is adhered to the skin of the breast to provide baseline measurements useable with signals from the sensor 20 to calculate changes in breast volume. FIG. 3 illustrates device 10 having been adhered to the breast 2. Illustrated in a phantom line is the location around which a girth (circumferential) baseline measurement is made. Additionally, an anterior-posterior (AP) baseline measurement of the protrusion of the breast 2 is made by measuring along the phantom line 36 from point 38 to point 40 on line 34, wherein the plane of the AP measurement is normal to the plane of the circumferential measurement.

Alternatively, the system can be used without the need to take baseline measurements, according to another embodiment of the present disclosure. In this embodiment, a user can input to the system the general breast cup size of the user to be measured, and use the cup size to calculate a volume estimate of the baseline breast. Further alternatively, no baseline measurements are taken and no entry of breast cup size is performed. Rather, the user inputs to the system when the user feels that the breast is full and also inputs to the system when the user feels the breast is feeling "empty", or relatively depleted of milk. At the times of entry of these full and empty inputs, the system takes a measurement of the breast and uses those relative subjective benchmarks to track full vs. empty state. The technology can also be benchmarked against the weight of the baby before feeding and after feeding without having to make any breast measurements at all.

Figure 33A:
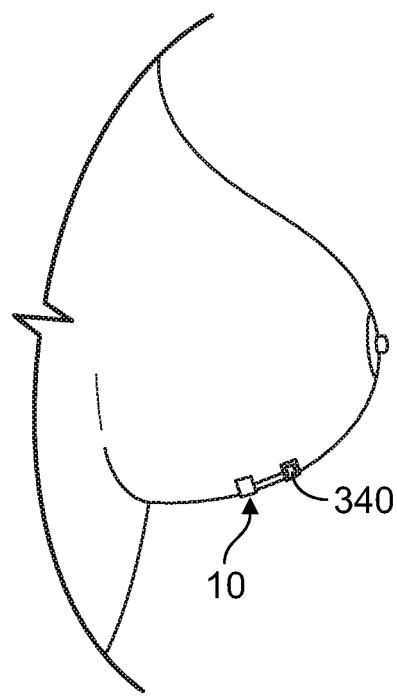
FIGS. 33A-33B illustrate a device including a pressure sensor, and placement of the device on the skin of a breast so as to be in contact with a supporting bra, according to an embodiment of the present disclosure.
Figure 33B:
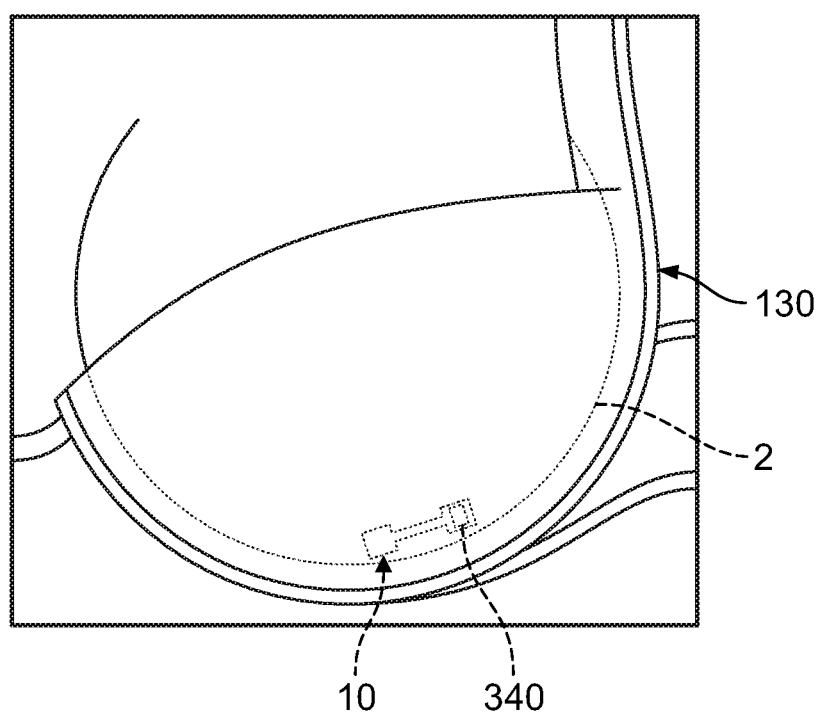

The orientation of device 10 as adhered to the breast can be important and be provided to the user in instructions for use of the device 10 and system. The preferred location for the device to be adhered to at present can be on the superior aspect of the breast 2 approximately half way between the collar bone and the nipple 3. For a device 10 that has bidirectional expansibility, one axis of expansibility should be lined up along the AP line and the other axis of expansiblity would then be naturally circumferentially oriented. One axis may only be needed and if so the axis shown through experimentation to be the most sensitive to changes and the sensors as well, these may ideally be placed at the base of the breast 2 against a region in contact with a supporting bra to add additional data regarding breast weight as well. The signal outputted by pressure sensor 340 (e.g., see FIGS. 33A-33B) representative of a pressure change between the breast 2 and the supporting bra 130, as illustrated in FIGS. 33A-33B. The pressure sensor 340 measures a force that is proportional to the change in breast size, which can be used to estimate volume change of the breast 2.

Figure 4:
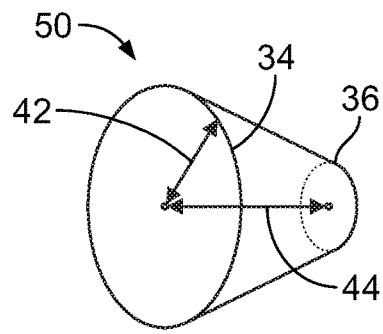
FIG. 4 illustrates a portion of the breast defined by the circumferential and AP measurements, according to an embodiment of the present disclosure

FIG. 4 illustrates a portion of the breast 2 defined by the circumferential and AP measurements. The volume of this portion can be calculated as the measurements 34 and 36, and the radii 42 and 44 are known.

For example, by modeling the breast as a hemisphere, as an approximation of the volume of the breast 2 but not as a real or precise reflection of the outer shape of a natural breast which does not correspond to a hemisphere, the initial volume contained in the half sphere would be:

$$V_1 = (2/3) * \Pi * r_1^3. \quad (1)$$

where
$V_1$ is the initial volume of the hemisphere in an initial state; and
$r_1$ is the radius of the hemisphere in the initial state.

To conform the breast 2 to the model, the initial circumference of the breast 2 measured at the base is $$C_1 = 2 * \Pi * r_1 \quad (2)$$

where
$C_1$ is the initial circumference of the breast 2 as measured; and
the length from the top of the sphere to the bottom along the arcuate path of the breast 2 (as measured by the initial AP measurement is $$L_1 = \Pi * r_1 \quad (3)$$

where
$L_1$ is the initial AP measurement of the base.

If the breast circumference is not measure at the base of the breast 2, a parallel equation can be derived for the location of measurement of the circumference of the breast, to scale it to an estimate of the measurement at the base of the breast 2.

When the volume of the breast changes (referred to here as $V_2$) the difference between the two states can be calculated if $r_1$ and $r_2$ (the radius of the breast model at $V_2$) are known or calculated. If only the change in length L or the change in circumference C are measured, $r_2$ as follows. Device 10 measures a portion of the total arc of the length (L) or circumference (C), so the the smaller change measured by the sensor (device 10) is extrapolated to the entire circumference $C_1$, as the initial circumference $C_1$ is known and the length of the expandable region (bridge 16) of the sensor (device 10) is known, both at $V_1$ and at $V_2$. The bridge 16 length is denoted as $s_1$ state 1 (i.e., where volume is $V_1$) and as $s_2$ at state 2 (when volume is $V_2$). Given $C_1$ is known, $C_2$ can be calculated as follows:

$$s_{1c} = C_1/a \quad (4)$$

where
$s_{1c}$ is the length of bridge 16 in the initial state (state 1, $V_1$); and
a is the arc (length of the portion of the circumference) measured by the device 10.

Now knowing the value of "a", $C_2$ can be solved for as follows:

$$S_{2c} = C_2/a \quad (5)$$

where
$s_{2c}$ is the length of bridge 16 in the changed volume state (state 2, $V_2$) as sensed and calculated by the system.

A similar approach can be used to calculate the length L in state 2, as L1 is known and the lengths of the bridge $s_{1L}$ and $s_{2L}$ in states 1 and 2 are sensed and calculated by the system.

The change in circumference between states 2 and 1 is calculated by $$C_2 - C_1 = a*(s_{2C} - s_{1C}) = 2*\Pi*(r_2 - r_1) \quad (6)$$

Since The $r_1$, $s_{1C}$, $s_{2C}$, and a are known, $r_2$ is calculated. This is then entered into the volume formula and volume is calculated as follows:

$$V_2 - V_1 = (2/3)*\Pi*(r_2^3 - r_1^3) \quad (7)$$

The device 10 can be calibrated by recording signals received from sensor 20 at different stages of breast feeding and the resultant changes in volume of the breast 2. By taking the circumferential 34 and AP 36 measurements at different times as the breast 2 changes in size resulting from expression of milk, a look up table can be generated that correlates the signals from the sensor 20 with specific volume changes in the breast 2. Further optionally, an algorithm can be derived from the successive measurements to develop a relationship between the sensor 20 signal and the change in volume of the breast 2, relative to the baseline circumferential 34 and AP 36 measurements.

The sensor 20 of device 1, in addition to or alternative to being configured for measuring displacement metric by stress/strain measurements, may be configured to measure either directly or indirectly at least one of: impedance changes; pressure changes; acoustic properties; weight; mass; density; compliance; electrical resistance; and/or capacitance metrics. One non-limiting way of measuring capacitance can be by use of a material that changes in capacitance as it is stretched, (e.g., sensors from StetchSense, Auckland, New Zealand) Once the metric(s) has/have been assessed or registered by the device 10, device 10 can communicate the metric(s) to an external computer via various different mechanisms. The embodiment shown in FIG. 1 is provided with one or more antennae 28. In one variant, a single antenna 28 is provided for receiving and transmitting signals to and from device 10. In another variant, a first antenna 28 is provided for transmitting signals and a second antenna 28 is provided for receiving signals. Device 10 can communicate with one or more external devices configured to interrogate the device 10, receive signals from the device 10 representative of measurements taken by sensor 20, and processing the signals to output a desired result, such as change in volume of the breast and an estimate of the milk volume having been expressed, which is calculated as a function of the change in breast volume. The milk volume expressed may be calculated as a one-to-one relationship with the change in breast volume, or as a function of the change in breast volume modified by a factor that can be empirically determined by taking actual measurements of the volumes of expressed milk and correlating them with the measurements received from the sensor 20.

Figure 5:
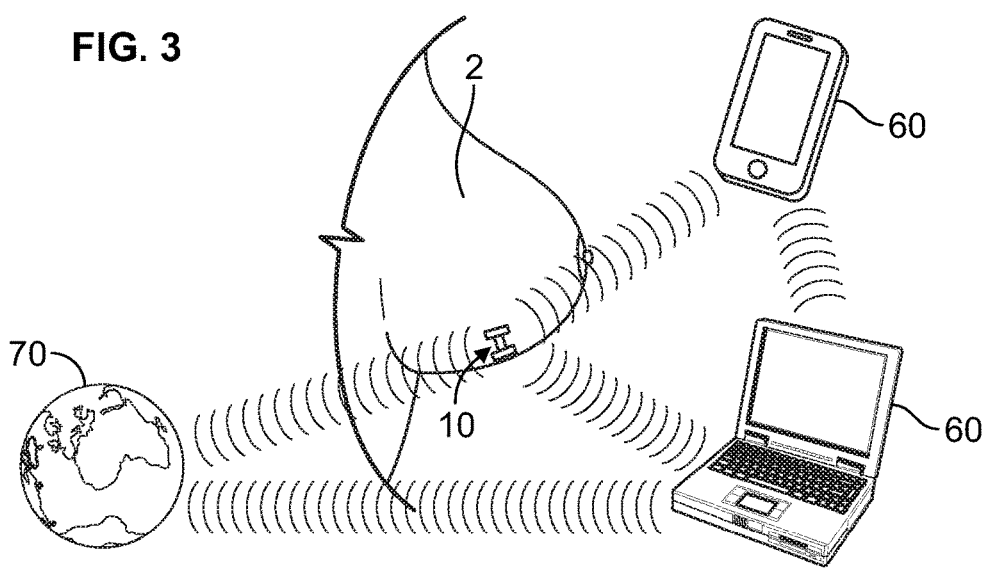
FIG. 5 shows that the signals from device of FIG. 1 can be wirelessly transmitted to one or more computers configured to process the signals, according to an embodiment of the present disclosure.

As noted above, the embodiment of FIG. 1 includes its own power source 24, so that data gathered by the device can be automatically transmitted to a preconfigured external device and/or uploaded to the internet, such as to a cloud-base server. FIG. 5 shows that the signals from device 10 can be wirelessly transmitted to one or more computers 60 configured to process the signals. Computer 60 can then retransmit the signals and/or output data resultant from processing the signals, to one or more additional computers 60 and/or a server on the internet 70. Alternatively, device 10 can transmit signals directly to all pre-designated external computers 60 and/or server(s) on the internet 70. In one particular embodiment, device 10 automatically transmits signals to a smartphone 60 or tablet 60 of the user as the measurements are taken.

The adhesive 18 of the device 10 maintains the adherence of the device 10 to the skin for at least a period of minutes, preferably for a period of days, up to at least a week. Thus, when the initial baseline measurements are made, they do not need to be re-accomplished for subsequent feedings, as long as the same device 10 remains adhered to the breast 2. Also, the system can estimate milk volume expression whether the feeding is a live breast feeding of a baby, or a milk extraction session performed using a breast pump. Devices 10 may each be encoded with a unique identification code, so that multiple devices 10 may be used at the same time (e.g., one on each breast 2) to allow volume changes in both breasts 2, as the external computer 60 can distinguish between the signals received from different devices 10 based upon their unique identifiers.

Figure 6:
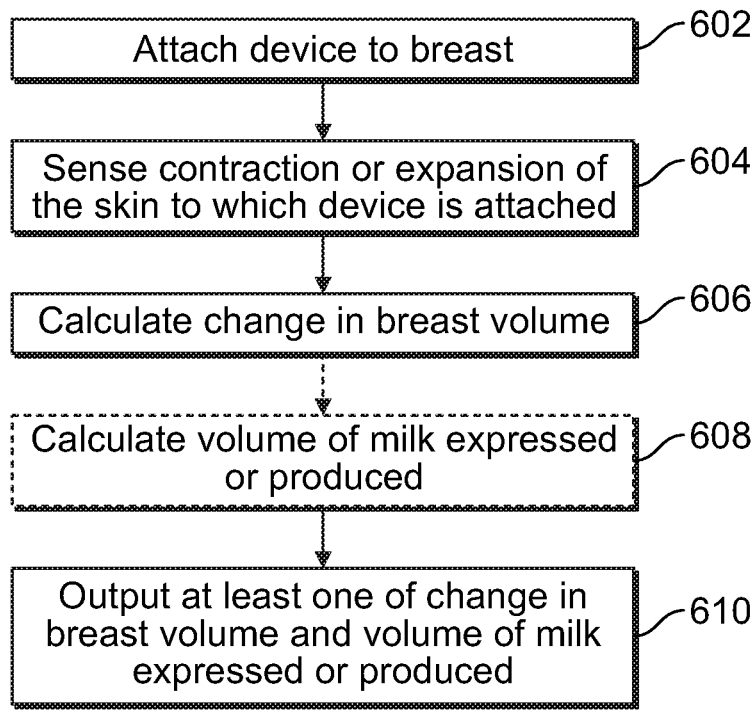
FIG. 6 illustrates events that may be carried out during a process of measuring a volume of milk expressed by a breast, according to an embodiment of the present disclosure.

FIG. 6 illustrates events that may be carried out during a process of measuring a volume of milk expressed by a breast 2. At event 602, device 10 is attached to the breast 2, preferably using an adhesive in a manner as described above. At event 604, an amount of contraction or expansion of the skin of the breast 2 to which device is attached is sensed. Sensing events may occur periodically at predetermined times, e.g., every minute, every five minutes, every ten minutes, or according to some other predetermined time scheme. Alternatively, device 10 may continuously sense changes in the breast volume, but only transmit signals representative of such measurements when pinged by an external computer 60, 70 that requests the signals.

At event 606 data from sensing contraction or expansion at event 604 is used to calculate a change in volume of the breast 2 that has occurred during the time from the previous sensing event to the present sensing event and/or from the time of initially attaching the device 10 to the breast and the present sensing event.

Optionally, at event 608, the volume of milk expressed or produced may be calculated based on the change in volume (contraction or expansion) of the breast calculated at event 606. At event 610 at least one of the change in breast volume and volume of milk expressed/produced are outputted for viewing by a user.

Figure 7:
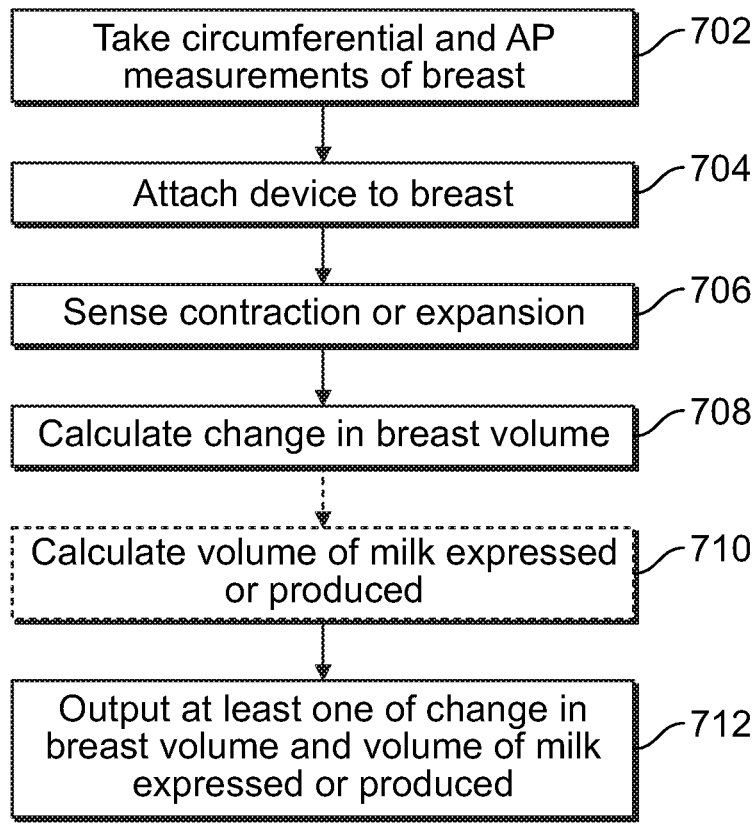
FIG. 7 illustrates events that may be carried out during a process of measuring a volume of milk expressed by a breast, according to another embodiment of the present disclosure.

FIG. 7 illustrates events that may be carried out during a process of measuring a volume of milk expressed by a breast 2 according to another embodiment of the present disclosure. At event 702, circumferential and AP measurements of the breast 2 are taken in a manner as described above. The circumferential and AP measurements are entered into a program run by a processor contained either on the device 10 itself, or, preferably on an external computer 60. The program calculates a starting volume of the breast 2 at (or near) the time that device 10 is attached to the breast.

At event 704, with prior to, or immediately after taking the circumferential and AP measurements, device 10 is attached to the breast 2, preferably using an adhesive in a manner as described above.

At event 706, an amount of contraction or expansion of the skin of the breast 2 to which device is attached is sensed. Sensing events may occur periodically at predetermined times, e.g., every minute, every five minutes, every ten minutes, or according to some other predetermined time scheme. Alternatively, device 10 may go into a sleep mode when no change in lengths has been sensed over a predetermined time, and reactivate when a change in length in one or both dimensions is again detected. A further alternative provides a pressure sensor within a supporting bra, so that changes in pressure against the bra caused by changes in volume of the breast 2 supported by the bra can be sensed and used to estimate volume change in the breast.

At event 708 data from sensing contraction or expansion at event 706 is used, together with the baseline data entered as the circumferential and AP measurements (and initial volume calculation) to calculate a change in volume of the breast 2 that has occurred during the time from the previous sensing event to the present sensing event and/or from the time of initially attaching the device 10 to the breast and the present sensing event.

Optionally, at event 710, the volume of milk expressed or produced may be calculated based on the change in volume (contraction or expansion) of the breast calculated at event 708. At event 712 at least one of the change in breast volume and volume of milk expressed/produced are outputted for viewing by a user.

Figure 8:
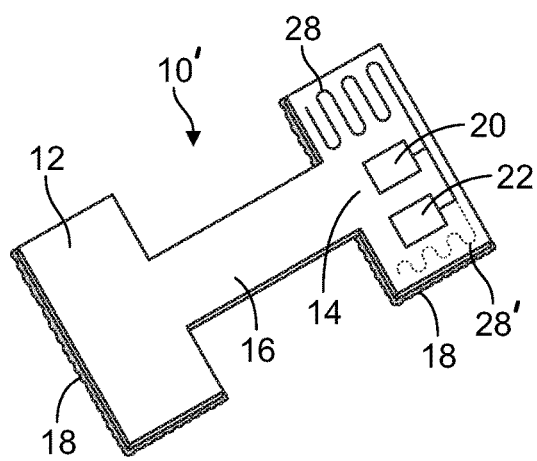
FIG. 8 is a perspective, schematic illustration of a device configured to be adhered to the skin of a subject to detect expansion and contraction of the skin, according to another embodiment of the present disclosure.

FIG. 8 is a perspective, schematic illustration of a device 10' configured to be adhered to the skin of a subject to detect expansion and contraction of the skin, according to another embodiment of the present disclosure. Device 10' includes a distal mount portion 12, a proximal mount portion 14 and a flexible intermediate portion 16 that bridges the proximal 14 and distal 12 mount portions. The proximal mount portion 14 has components mounted to it that measure changes in the skin that the device 10 is adhered to. The back surfaces of the distal and proximal mount portions 10, 12 have an adhesive 18 applied thereto so that the device 10 can be adhered to the skin, while the intermediate (bridge) portion 16 does not have any adhesive applied thereto, so that it can more freely expand and contract.

The distal and proximal mount portions 12, 14 are adhered to the skin at locations that initially place the bridge portion 16 in an unbiased state (neither stretched nor compressed). A sensor 20, such as an electronic resistor, strain gauge, magnet or the like is provided on proximal mount 14 and is configured so that compression and expansion of the bridge portion 16 applies strain/forces to the sensor 20, which measures the amount of expansion or compression according to methods well understood in the strain measurement arts. In the embodiment shown in FIG. 1, a circuit 22 is provided on proximal mount 14 that is powered by an external computing device 60 and can be configured to process the output of the sensor 20, and send processed signals representative of the output of sensor 20 to the external device 60 via antenna 28. Like the embodiment of FIG. 1, the transmission is wireless, and may be accomplished, for example, via BLUETOOTH® transmitter or radio transmitter of the type used in cellphones, such as 2G, 3G or 4G. In another approach, a circuit capable of being powered by a body motion or body heat can be incorporated into the device. Antenna 28 can be used to both receive signals and power from the external computer 60 and to transmit signals to the external computer 60. Alternatively, a first antenna 28 may be provided for receiving and sending signals, with a second antenna 28' (shown in phantom in FIG. 8) used to receive power from the external computer 60. Upon being activated by the external computer 60 device 10 takes a measurement with sensor 20 and circuit 22 receives the measurement data from the sensor, processes the data and sends it to the external computer via antenna 28.

Figure 9:
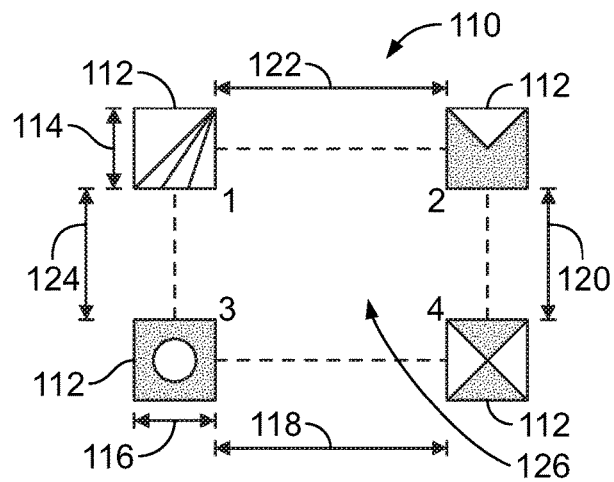
FIG. 9 is a schematic illustration of a device configured to be adhered to the skin of a subject for use in detecting expansion and contraction of the skin, according to another embodiment of the present disclosure.

FIG. 9 is a schematic illustration of a device 110 configured to be adhered to the skin of a subject for use in detecting expansion and contraction of the skin, according to another embodiment of the present disclosure. Device 110 includes a plurality of marker elements 112 of known dimension, both of height 114 and width 116. Although the markers 112 shown in FIG. 9 are all of the same height 114 and width 116, this is not necessary, as long as the height and width of each is known. Although the markers 112 can be individually adhered to the tissue at known distances 118, 120, 122, 124 apart from each other, it is more convenient to provide the markers 112 on a main body or backing 126 which is transparent, white, or some other color scheme that is readily distinguishable from the markers 112, as this makes application of a single unit to the skin much easier and the markers 112 will be less prone to be applied at distances other that what they are intended to be applied at. Although the distances 118, 120, 122 and 124 are shown in FIG. 9 as all being equal, this is not necessary, as they can be unequal, as long as they are known. Nor is the number of markers 112 limited to four, as more or fewer markers can be employed to carry out the same functions. Also, by providing each of the markers to have a different pattern, as shown, this assists in determining the orientation of each marker as it moves due to stretching or shrinking of the skin of the breast 2, which facilitates differentiation between circumferential measurements and longitudinal (AP) measurements, so that comparative subsequent measurements are properly referenced each time a "picture" is taken.

Figure 10:
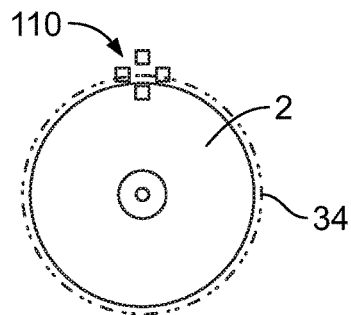
FIGS. 10-11 illustrate the device of FIG. 9 having been adhered to a breast, according to an embodiment of the present disclosure.
Figure 11:
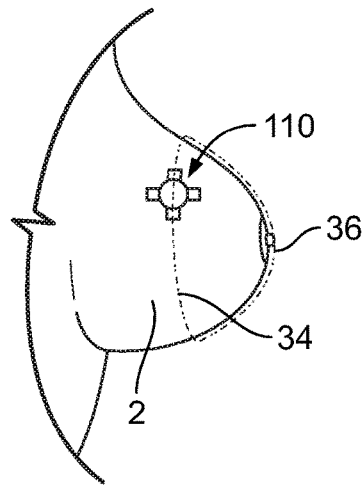

FIGS. 10-11 illustrate device 110 having been adhered to a breast 2. Once the device 110 is attached to the breast, both circumferential 34 and AP 36 measurements are taken of the breast 2 in its current state to create baseline data as to the volume of the breast 2 in the same manner as discussed previously. Since the distances 118, 120, 122, 124 between the marker elements 112 are known at baseline, small changes between the distances that occur when the breast 2 expands or contracts can be detected. Because the marker elements 112 themselves are fixed in dimension, any visual distortion can be accommodated for, by adjusting visual results to normalize the viewed dimensions of the markers 112 to their known dimensions, and also applying proportional correction to the viewed distances 118, 120, 122, 124. This keeps track of scale, as the camera may be placed at varying angles and distances relative to the marker elements when taking successive pictures. By comparing measurements of the distances 118, 120, 122, 124 relative to the initial distances that correspond to the baseline volume, a change in volume can be calculated.

Figure 12:
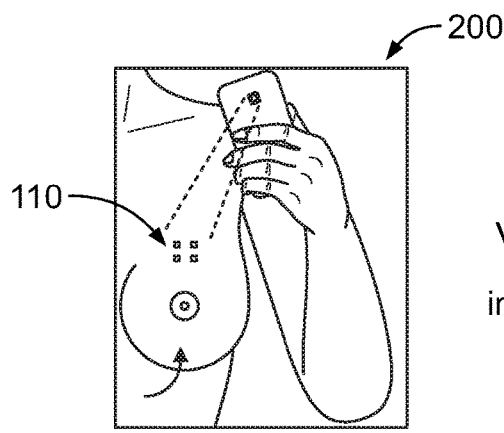
FIG. 12 illustrates a system used to detect volume changes in a breast and to calculate an estimate of milk volume expressed from the breast as well as milk volume produced, as the breast re-expands, according to an embodiment of the present disclosure.

FIG. 12 illustrates a system 200 used to detect volume changes in the breast 2 and to calculate an estimate of milk volume expressed from the breast 2 as well as milk volume produced, as the breast 2 re-expands. In FIG. 12, device 110 has been adhered to the breast 2 in a manner as already described, and the circumferential and AP measurements have already been taken and inputted to an app running on the smartphone 60. Although a smartphone 60 is shown in FIG. 12, it is noted that a tablet computer or laptop computer having a camera could alternatively be used in the system to perform the monitoring and calculating. Further alternatively, any digital camera could be used and the digital image formed by the camera could be uploaded to a computer running the app for breast volume and milk production calculation. Further alternatively, changes in the distances 118, 120, 122, 124 could be manually measured, such as with calipers or some other mechanical measuring device and manually inputted to the app of the external computer, or some other automated means of measuring the changes in distances could be employed. Marks made directly on the skin with a pen or other writing utensil, or marks associated with a tattoo, ink stamp, or stencil or the like, can be photographed and distances between sub-parts of the various images can be tracked such as by uploading the images to a computer. Baseline information can be created by taking the photos of the images at known times such as when the breast is deemed to be full, or empty or in some other known state or on a specific timetable. Image patterning can be employed to assess multiple dimensions of distance changes, and can help in correcting or tracking camera orientations. Camera orientations can also be determined with the aid of an accelerometer. Recalibrations are contemplated after single or multiple uses. Still further alternatively, rather than taking actual "pictures", the image of the sensors 112 can be directly determined by an app, such through a camera of a smart phone or other computer device equipped with scanning capability, wherein a photo is never saved, but rather the pixels are directly inputted to the processor (app or other application running on the processor), similar to the way that a bar code is currently processed by scanning. Once the elements of the image are collected the data is kept with no remaining visual data.

An image is next taken of the device 110 by the external computer 60 and initial breast volume is calculated by the processor of the computer 60 running the app configured to calculate breast volume. The computer 60 saves the initial breast volume and records time and date that this initial measurement was made, plus other related information, such as which breast 2 was measured. Additionally, the user may input further related information, such as what state the breast 2 was in when taking the measurement (e.g., pre- or post-breast feeding, pre-or-post-breast pumping, etc.)

Further images can be taken with computer 60 to establish a record of milk production and milk expression during feedings/pumpings. The user can enter any other notes as desired, that correspond to each additional image. The device 110 can be left adhered to the breast 2 for as long as the adhesive will hold, typically a few days to a few weeks, but could be a shorter or longer time. As long as the device 110 remains adhered to the breast 2, images can be taken and volumes calculated whenever desired, without the need to take further baseline measurements. If upon losing or removing the device 110, another device 110 can be re-applied and, if re-applied immediately after removal or loss of the previous device 110, there is no need to take new baseline measurements.

Figure 13:
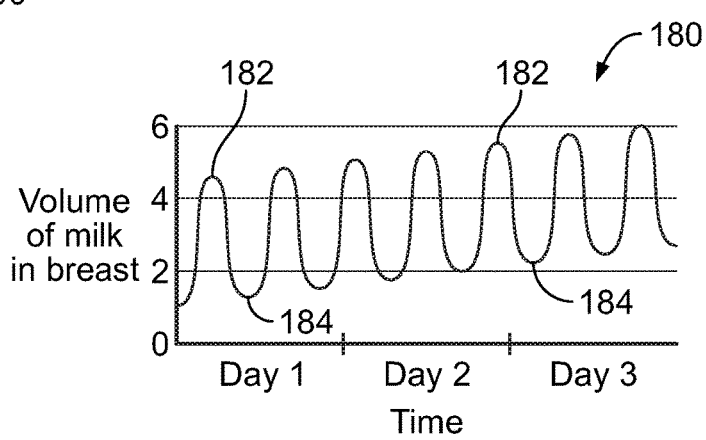
FIG. 13 is a schematic representation of one type of graph that can be visually represented on the display of the external computer and/or printed out for viewing by a user, after taking a series of measurements/images of the breast at different conditions of pre- and post-feeding/pumping, according to an embodiment of the present disclosure.

FIG. 13 is a schematic representation of one type of graph that can be visually represented on the display of the external computer 60 and/or printed out for viewing by a user, after taking a series of measurements/images of the breast 2 at different conditions of pre- and post-feeding/pumping. Graph 180 shows calculated milk volume levels in a monitored breast 2 over a period of three days, with the peaks of the graph 180 being milk volume values calculated for the breast 2 prior to breast feeding or breast pumping at the times indicated and the valleys 184 being milk volume values calculated for the breast just after feeding/pumping. The difference between a peak value 182 and a valley value that immediately follows that peak value is the calculated volume of milk consumed by the baby or pumped. Over time, this graph shows that the volume of milk being produced by the breast 2 is increasing, and the volume consumed or pumped is also increasing.

Figure 14:
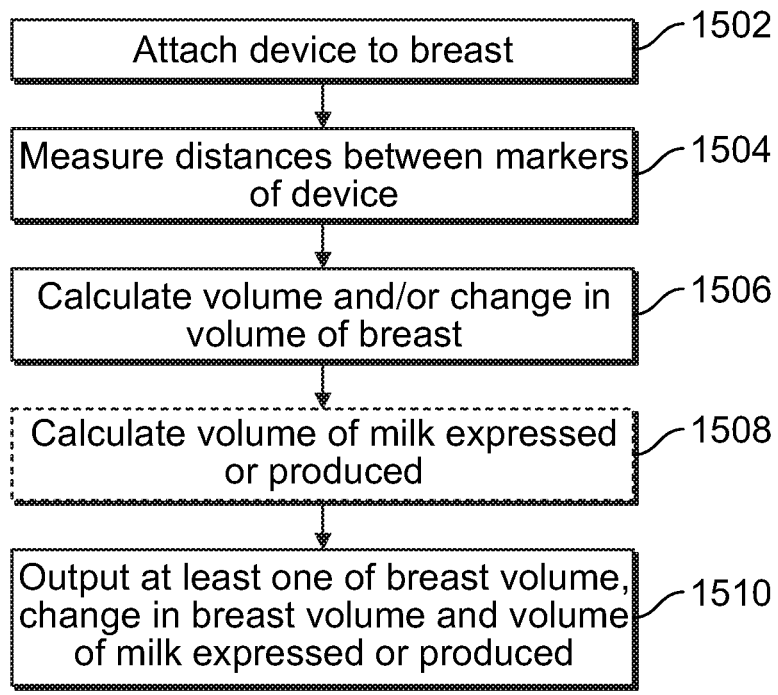
FIG. 14 illustrates events that may be carried out during a process of measuring a volume of milk contained in a breast, according to another embodiment of the present disclosure.

FIG. 14 illustrates events that may be carried out during a process of measuring a volume of milk contained in a breast 2, according to another embodiment of the present disclosure. At event 1502, device 110 is attached to the breast 2, preferably using an adhesive.

At event 1504, an amount of contraction or expansion of the skin of the breast 2 to which the device is attached is sensed by measuring the change in distance between markers of the device, using an external implement. In a preferred embodiment, this measurement is taken by shooting a photo of the device using an external camera and loading a digital representation of the photo into an app run by an external computer which measures the distances and calculates a volume. Sensing events may occur periodically at predetermined times, e.g., every minute, every five minutes, every ten minutes, or according to some other predetermined time scheme.

At event 1506 data from measuring the distances between markers of the device is used to calculate a volume or change in volume of the breast 2.

Optionally, the volume of milk expressed or produced may be calculated based on the change in volume (contraction or expansion) of the breast calculated at event 1506. At event 1510 at least one of the breast volume, change in breast volume and volume of milk expressed/produced are outputted for viewing by a user.

Figure 15:
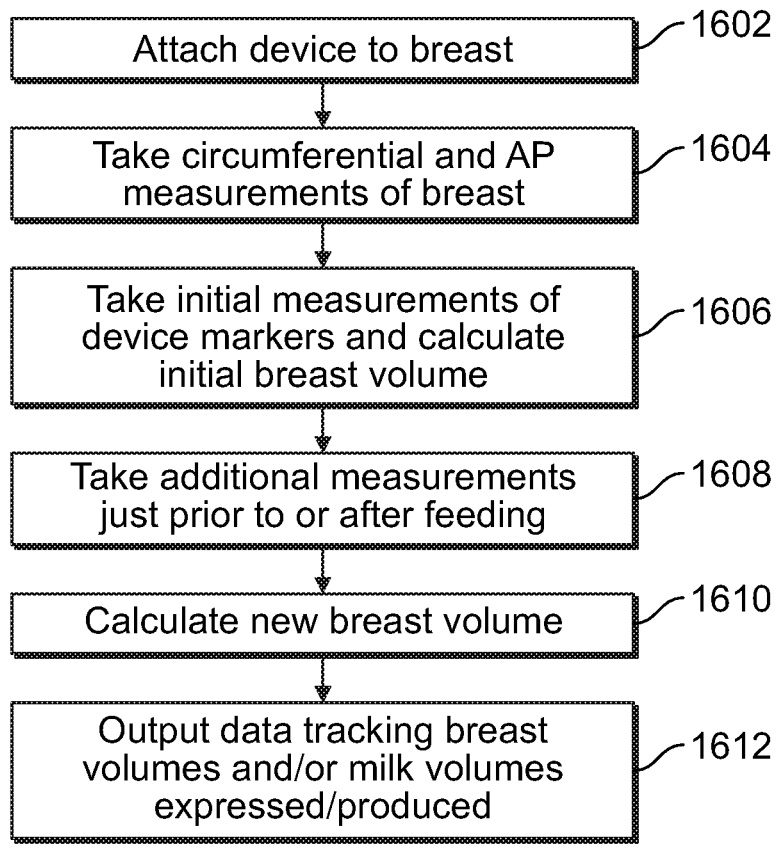
FIG. 15 illustrates events that may be carried out during a process of calculating a volume of a breast, change in volume of a breast and/or volume of milk expressed or produced by a breast according to another embodiment of the present disclosure.

FIG. 15 illustrates events that may be carried out during a process of calculating a volume of a breast, change in volume of a breast and/or volume of milk expressed or produced by a breast 2 according to another embodiment of the present disclosure. At event 1602, the device 110 is attached to the breast 2, preferably using an adhesive in a manner as described above.

At event 1604 circumferential and AP measurements of the breast 2 are taken in a manner as described above. The circumferential and AP measurements are entered into a program run, such as an app by a processor of an external computer 60.

At event 1606 the distances between device markers 112 after attachment to the breast 2 are measured. To make these initial measurements, preferably a photographic image is taken, using a camera of the external computer 60, which then automatically inputs the image data to the app running on the external compute for further processing. Alternative methods of making the initial measurements can be performed, as described above. An initial breast volume is calculated by the processor of the computer 60 running the app configured to calculate breast volume, using the baseline data from the circumferential and AP measurements and the distance data obtained during event 1606. The computer 60 saves the initial breast volume and records time and date that this initial measurement was made, plus other related information, such as which breast 2 was measured. Additionally, the user may input further related information, such as what state the breast 2 was in when taking the measurement (e.g., pre- or post-breast feeding, pre-or-post-breast pumping, etc.)

At event 1608, after a period of time has passed, additional measurements of distances between the markers 112 are performed, such as just prior to breast feeding or pumping, or just after breast feeding or pumping. Using the data obtained from the additional measurements, a new breast volume can be calculated. Additionally, the app may calculate change in breast volume from the previous calculation, as well as estimate a milk volume that corresponds to the calculated breast volume. The calculated values are saved in memory of the computer 60. Events 1608 and 1610 can be iterated pre- and post-each breast feeding/pumping to keep a track record of milk volume produced and expressed.

At event 1612, the external computer may display and/or print out or otherwise output the calculated breast volume data and associated times during which the breast volumes were calculated. Further optionally, the output may include calculated estimates of milk volume consumed by a feeding baby, total milk volume expressed by the breast 2, milk volume expressed during breast pumping, etc.

Figure 16:
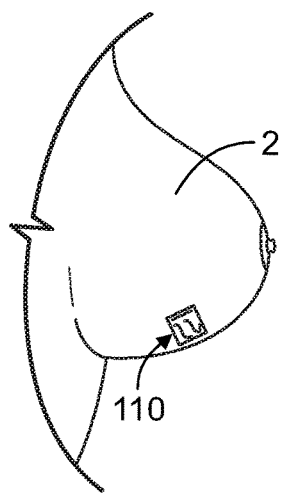
FIG. 16 shows a device applied to a breast according to another embodiment of the present disclosure.
Figure 17:
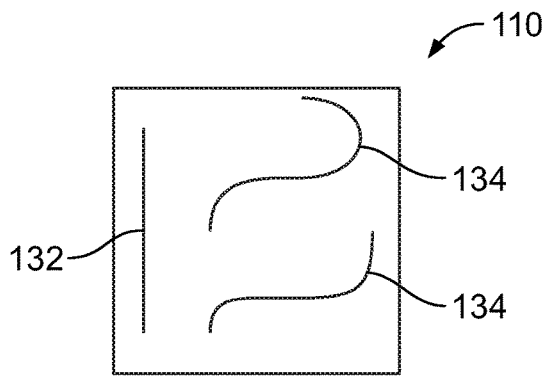
FIG. 17 is an isolated view of the device shown in FIG. 16.

FIG. 16 shows a device 110 applied to a breast 2 according to another embodiment of the present disclosure. FIG. 17 is an isolated view of device 110 shown in FIG. 16. In this embodiment, device 110 includes a fixed marker 132 on a portion of the device that is configured to neither expand or contract when the skin to which it is attached expands or contracts. One or more expansile markers 134 are also provided on the device and are configured to expand and contract along with expansion and contraction of the skin to which the device 110 is attached. The expansile markers 134 can be made of different materials than that from which the fixed marker 132 is made, similar to the manners described above with regard to portion 16 versions portions 12 and 14 in FIG. 1. Also similar to the description of FIG. 1, the fixed marker 132 may be on a portion of the device 110 that does not stretch to maintain orientation/distance and other portions of the device are made of material that does change dimension/orientation that correlates with some measure that correlates with volume calculations.

Figure 30:
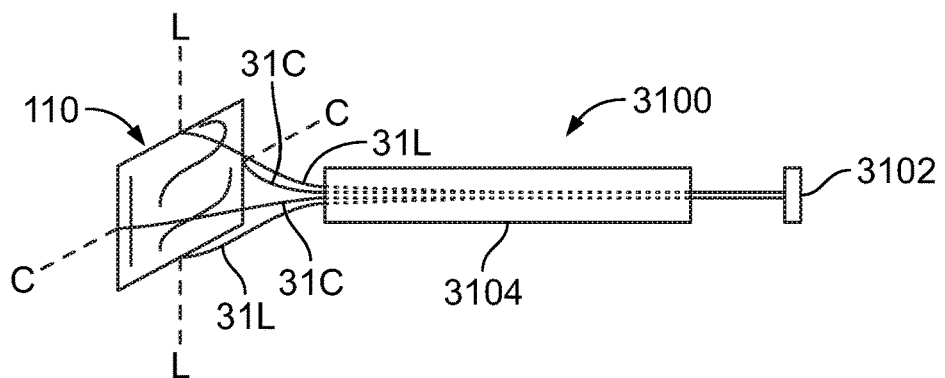
FIG. 30 illustrates an applicator according to an embodiment of the present disclosure.
Figure 31:
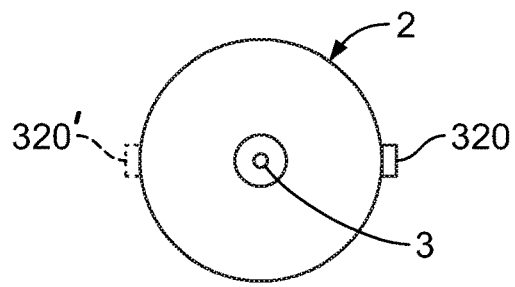
FIG. 31 illustrates an acoustic sensor attached to the breast to be used for estimating volume of the breast, according to an embodiment of the present disclosure.

The device 110 maybe placed with an applicator, such that there may be some "built in" stretch of the device 110 on the applicator itself, allowing the device 110 to decrease in size if the breast 2 decreases in size and thus has capability not only to measure stretch of the skin of the breast 2, but also contraction of the skin of the breast 2. This is also true of device 10. Of course, it is recommended to apply the device 10, 110 at a time that the breast is most empty and therefore at its smallest volume, as this would not require the device 10, 110 to be pre-stretched prior to attaching it to the breast 2. FIG. 30 illustrates an applicator 3100 according to an embodiment of the present disclosure. It is noted that other types of applicators that can accomplish the same functions described herein may be substituted for applicator 3100. Such applicator will have the ability to temporarily attach to a device 110 or 10 at locations so that it can pre-stretch the device 10, 110 prior to attaching it to the breast. The amount of pre-stretching may be pre-determined by a predetermined amount of stretching force applied by the applicator in both the circumferential (axis C-C) and length (AP. axis LL-as shown in FIG. 31) directions. Alternatively, the amount of stretching force applied may be variable, as in the case of applicator 3100 in FIG. 30, where the further that the actuator 3102 is pushed toward the main body 3104 of the actuator 3100, the further apart the actuator arms 31L extend apart from one another, and likewise the actuator arms 31C, thus providing variably increasing stretching force to the device 110, 10.

All points along the markers 132, 134 are mapped and inputted to the program (such as an app or other program) running on the external computer, so that distances between all points along the marker 132 and all points along the marker(s) 134 are known in the initial state, when the device is neither stretched (expanded) nor compressed, which is the condition of the device 110 prior to attaching it to the skin. After attachment to the skin, when the skin expands or contracts, the marker(s) 134 expand(s) or contract(s) by the same or some known proportional amount as the skin, while marker 132 remains in its original condition, neither expanded nor contracted.

Figure 18:
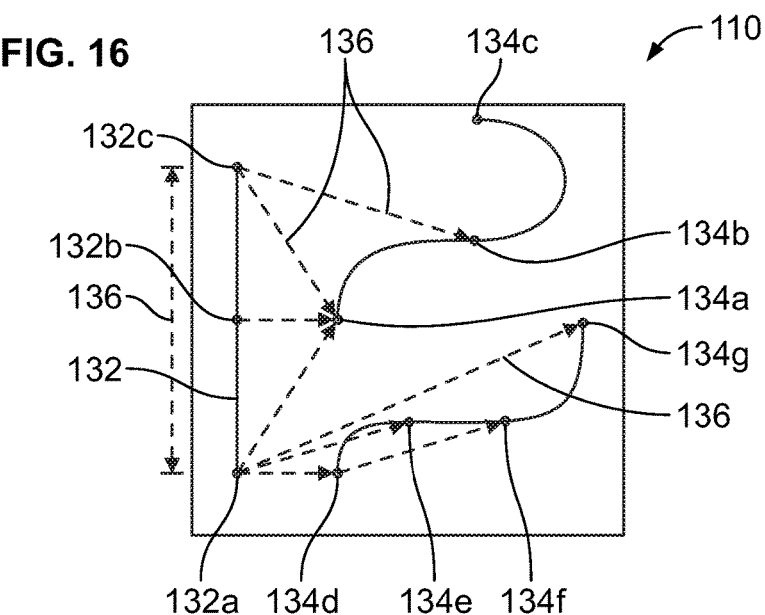
FIG. 18 is another view of the device of FIG. 17.

Because the length 136 (See FIG. 18) and width (negligible in this example) of marker 132 are known and the original distances between markers 132, 134 along all points are known, the amount of expansion of the skin can be readily determined by comparing distances measurements between points along the markers 132 and 134 and finding the changes in distance from the unbiased condition to the expanded or contracted condition. The distances between one of more points along the fixed marker 132 (points 132a, 132b and 132c in FIG. 18, but could be as few as one, or as many as desired or as practical to process depending upon the computing power available) and one or more points along the expansile markers 134 (134a-134g as shown, but could be as few as one per marker 134, or as many as desired or as practical to process depending upon the computing power available) are computed to determine the amount of expansion or contraction of the skin, which can then be used to calculate breast volume or change in breast volume, in embodiments where device 110 is applied to the skin of the breast. As the length 136 is known and remains fixed, this can be applied as a reference for all other distance measured, e.g., vectors 136 as illustrated in phantom in FIG. 18. Note that all vectors 136 have not been illustrated, for clarity of illustration. By knowing the original orientation of the device 110 on the skin and the length and directionality of the vectors 136, any one of the vectors 136 can be used to calculate the amount of expansion of the skin in any direction desired. In the case of breast 2 measurement, any vector 136 can be broken down into component vectors parallel to the planes of the circumferential and AP measurements to determine the amount of expansion or contraction of in the circumferential and AP planes. This can then be used, along with the baseline measurements to determine breast volume and change in breast volume. It could also be used to detect whether the breast 2 emptied uniformly or whether there may be some residual milk in one region or another based on the non-uniformity of the tension or relaxation.

As noted previously, all devices described herein can be applied to any skin location where it is desired to determine the amount of expansion or contraction of the skin. In one alternative example, device 110, or any of the other devices for attachment to the skin described herein, can be applied to the skin over a baby's stomach to detect changes in stomach volume. Measurements of skin contraction or expansion in this instance can be calibrated during feeding of the baby with a known volume of milk, such as by bottle feeding.

Figure 19:
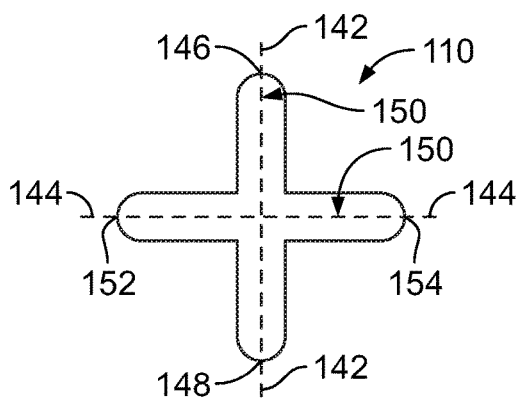
FIG. 19 illustrates a device that can be attached/adhered to the skin to measure skin contraction and expansion according to another embodiment of the present disclosure.

FIG. 19 illustrates a device 110 that can be attached/adhered to the skin to measure skin contraction and expansion according to another embodiment of the present disclosure. In this embodiment, device 110 is expansile and is designed to extend along two main axes 142, 144 that are orthogonal to one another. When applied to a breast 2, device 110 can be attached to the skin of the breast so that axis 142 is aligned with the circumferential plane used to perform the initial circumferential measurement of the breast 2 for the baseline data. In this way, measurement between the end points 146, 148 of device 110 along the axis 142 provides a measurement of the expansion of the breast 2 in the circumferential direction. By measuring the angle 150 between axis 142 and 144 after the skin has expanded or contracted, and measuring the distance between end points 152, 154 along the axis 144, the amount of contraction or expansion in the AP direction can be calculated. These changes in distance along the circumferential and AP directions can then be used together with the baseline measurements to calculate breast volume and or change in breast volume, as well as to calculate milk volume and/or change in milk volume in the breast 2.

Figure 20:
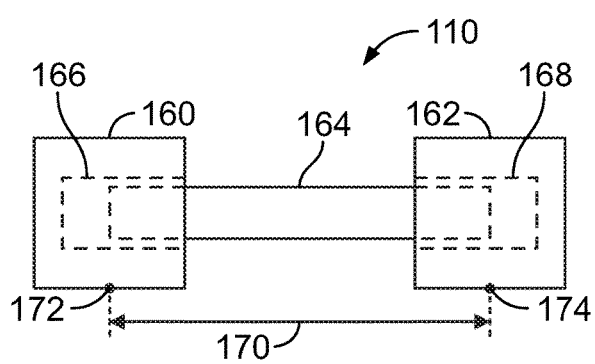
FIG. 20 illustrates a device that can be attached/adhered to the skin to measure skin contraction and expansion according to another embodiment of the present disclosure.

FIG. 20 illustrates a device 110 that can be attached/adhered to the skin to measure skin contraction and expansion according to another embodiment of the present disclosure. In this embodiment, first and second fixed markers 160, 162 are attached to the skin, with a bridge element 164 slidably received in channels 166, 168 of fixed marker elements 160, 162, respectively. As the skin expands or contracts, the elements 160, 162 that are fixed to the skin move with the skin. The bridge element 164 is not fixed to the skin and slides in or out of the channels 166, 168 as the elements 160, 162 move closer together or farther apart. By measuring a distance 170 between fixed points 172, 174 on the elements 160, 162 before and after skin expansion or contraction (such as by taking photo images, or manual measurement, like described with regard to the previous embodiments of device 110), a difference in the distance between points can be calculated and, together with baseline data, be used to calculate breast volume, change in breast volume, milk volume in the breast and change in milk volume in the breast.

Alternatively, any of the device 110 can be calibrated by taking measurements as described and correlating them to actual volumes of milk expressed from the breast, such as can be obtained during breast pumping, for example.

In further alternative embodiments, device 110 can be configured with electronic components to form an active sensor that sends signals to an external computer 60, like the embodiments of device 10 in FIGS. 1 and 8, for example.

Any of the devices described herein that are configured to actively send data to an external computer 60 can be configured to send an alert to the external computer, or the external computer 60 can be configured to generate an alert if a predefined abnormality in the data is present, such as, but not limited to: a missed feeding; a milk production change greater or less than a predetermined or average milk production change over a predefined time; enlargement of the breast 2 beyond a predefined volume; etc.

Figure 21:
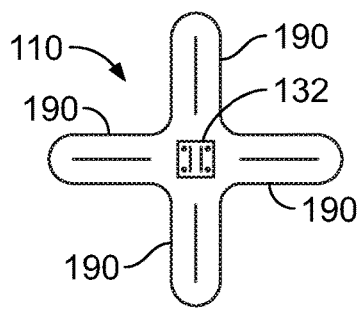
FIG. 21 illustrates a device that can be attached/adhered to the skin to measure skin contraction and expansion according to another embodiment of the present disclosure.

FIG. 21 illustrates a device 110 that can be attached/adhered to the skin to measure skin contraction and expansion according to another embodiment of the present disclosure. In this embodiment, device 110 is shaped like the embodiment of FIG. 19, but includes a marker 132 at the center that is configured to neither expand or contract when the skin to which it is attached expands or contracts. The arms 190 of device 110 are expansile and are configured to expand and contract along with expansion and contraction of the skin to which the device 110 is attached. Like the embodiment of FIG. 18, because the dimensions of fixed marker 132 are known, and the starting dimensions (prior to expanding or contraction) of the arms 190 are known, the amount of expansion or contraction of arms 190 can be calculated, using the dimensions of marker 132 as a reference.

Figure 22:
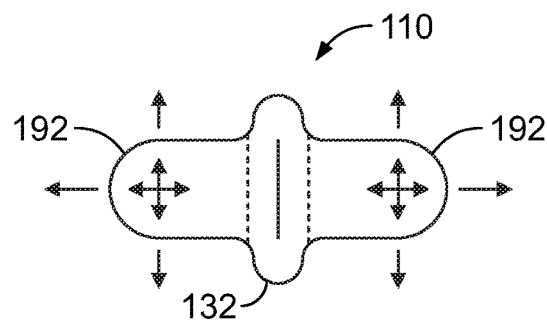
FIG. 22 illustrates a device that can be attached/adhered to the skin to measure skin contraction and expansion according to another embodiment of the present disclosure.

FIG. 22 illustrates a device 110 that can be attached/adhered to the skin to measure skin contraction and expansion according to another embodiment of the present disclosure. This embodiment is similar to the embodiment of FIG. 21, as it has a fixed marker 132 in the center that is configured to neither expand nor contract as the skin expands. Device 110 of FIG. 22 includes a pair of expansile arms, the expansion or contraction of which can be measure along both the circumferential and AP directions.

Figure 23:
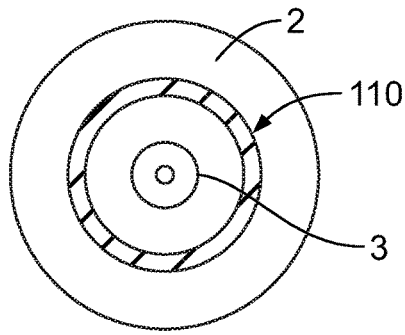
FIG. 23 illustrates a device that can be attached/adhered to the skin to measure skin contraction and expansion according to another embodiment of the present disclosure.

FIG. 23 illustrates a device 110 that can be attached/adhered to the skin to measure skin contraction and expansion according to another embodiment of the present disclosure. In this embodiment, device 110 comprises an expansile ring that is attachable/adherable to the breast 2 to encircle a portion of the breast 2. As the nipple 3 remains substantially unchanged during expansion and contraction of the breast 2 (except during feeding), by measuring the diameter of the nipple 3, it can be used as a reference point against which contraction and expansion of ring 110 can be measured.

Figure 24A:
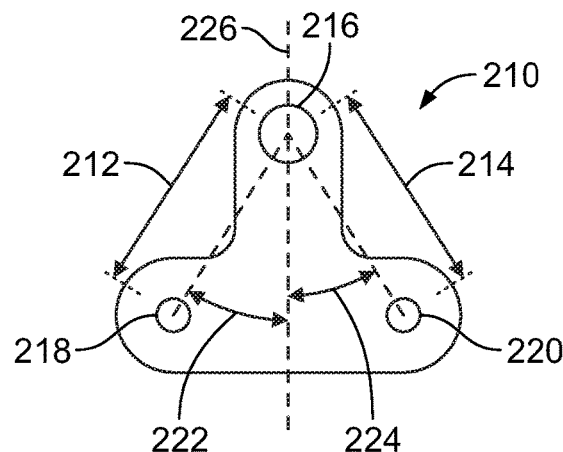
FIG. 24A shows a tool that can be used to apply marks to the breast at a fixed distance and orientation from a reference point, according to an embodiment of the present disclosure.

FIG. 24A shows a tool 210 that can be used to apply marks to the breast at a fixed distance and orientation from a reference point, such as the center of the nipple 3, for example. Tool 210 is made of flexible material so that it can readily conform to the curvature of the breast 2 as it is overlaid on the breast 2 to make the marks. The distances 212, 214 between the reference location 216 and the locations 218, 220 where the marks are to be made are pre-defined and pre-measured, as are the angles 222 and 224 of the lines connecting 216 and 218, and 216 and 220, respectively, relative to the longitudinal axis 226. As shown, the distances 212, 214 are equal, and the angles 222, 224 are equal and opposite, but neither the distances or the angles need be equal, only all must be known.

Figure 24B:
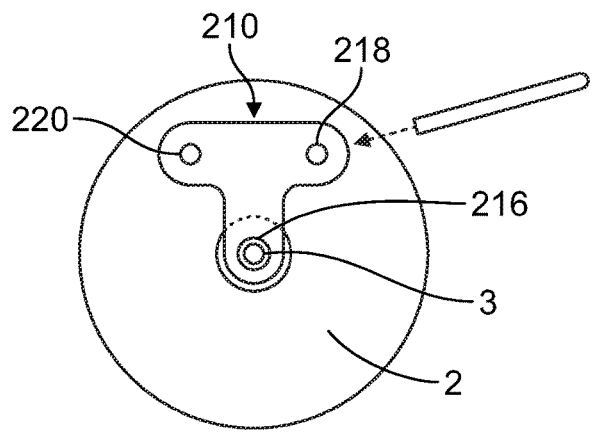
FIG. 24B illustrates tool overlaid on a breast to perform marking, according to an embodiment of the present disclosure.
Figure 24C:
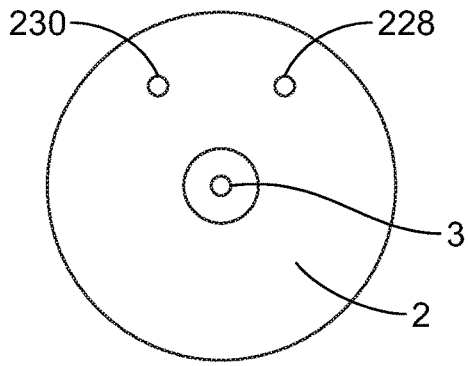
FIG. 24C illustrates the marks that remain after completion of the marking process and removal of the tool, according to an embodiment of the present disclosure.

FIG. 24B illustrates tool 210 overlaid on a breast 2 to perform marking and FIG. 24C illustrates the marks 228, 230 that remain after completion of the marking process and removal of the tool 210. The marks 228, 230 can be made with any type of marker that is safe and approved for marking the skin and which is visible. The nipple 3 can be used as a fixed reference to measure expansion and contraction distances of markers 228, 230 therefrom, in the same manner as described above with regard to FIG. 23. Although the tool 210 has been shown to make marks on the top portion of the breast, it is noted that the marks 228, 230 could be made on the bottom portion of the breast 2 a side portion of the breast, or at any radial angle from the nipple 3, relative to the circumference of the breast 2

Figure 25:
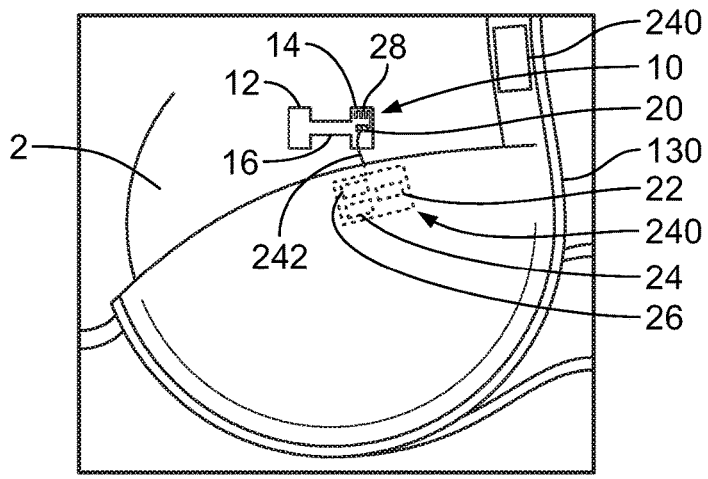
FIG. 25 illustrates a device that is used in combination with a power unit that is electrically connectable and detachable from the device via an electrical connection wire (or wireless connection), according to an embodiment of the present disclosure.

FIG. 25 illustrates a device 10 that is used in combination with a power unit 240 that is electrically connectable and detachable from device 10 via an electrical connection wire 242 (or wireless connection), according to an embodiment of the present disclosure. Device 10 operates like the embodiment of device 10 described with regard to FIG. 1, but the battery 24, optional memory 26 and control circuit 22 are provided on power unit 240. This makes device 10 less expensive to manufacture to facilitate its production as a disposable unit. The relatively more expensive control circuit, battery and memory are reusable, as they can readily be detached or otherwise electrically disconnected from one device 10 and attached or otherwise electrically connected to another device10. An alternative mounting location for the power unit is shown on the strap of the bra 130.

Figure 26:
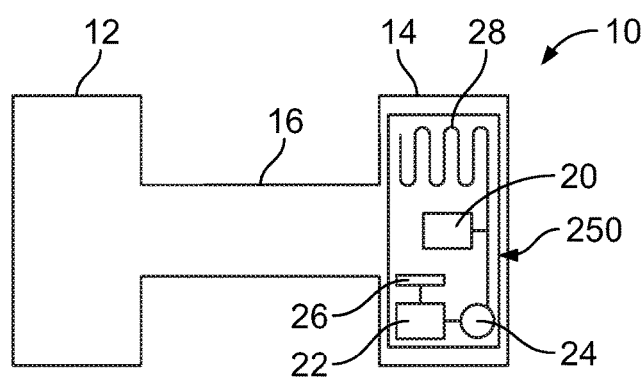
FIG. 26 illustrates a device according to another embodiment of the present disclosure.

FIG. 26 illustrates a device 10 according to another embodiment of the present disclosure. The embodiment shown is like that of the embodiment of FIG. 1, except that one or more of the electronic components (all, as shown, but could be fewer than all) are provided on a substrate 250 that is detachable from the proximal portion 14. This allows the patch portions 12, 14, 16 to be made disposable, while the substrate and its components can be reusable, being detachable from one patch and reattachable to another patch, thereby saving costs. It is noted that this same principle can be applied to any of the other device that include electronic components, such as the embodiment shown in FIG. 8.

Figure 27:
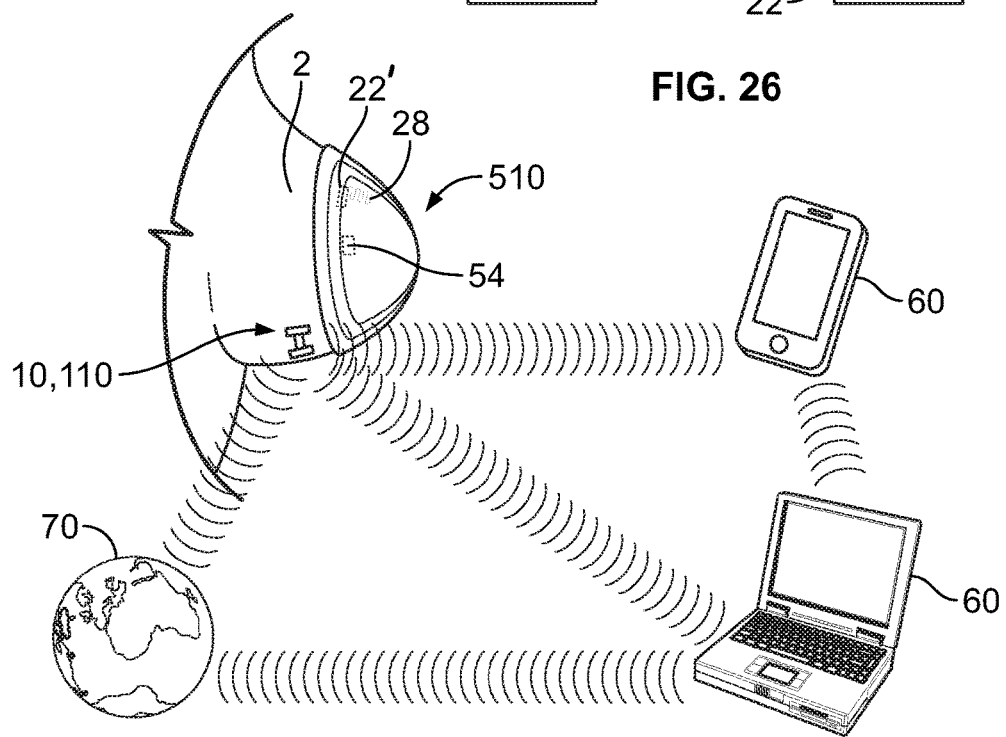
FIG. 27 illustrates a system that can be used for calculating and monitoring breast milk production and expression according to an embodiment of the present disclosure.

FIG. 27 illustrates a system that can be used for calculating and monitoring breast milk production and expression according to an embodiment of the present disclosure. In addition to the methods and devices described with regard to the system shown in FIG. 5, a breast pump 510 can be integrated into the system so that breast milk expression can be tracked by breast pump 510 during breast feeding, if desired, and integrated into the data calculated and tracked using the software on the external computer 60. It is noted that this is optional, as milk production and expression can be monitored and calculated using device 10 or 110 (or other disclosed devices) and the associated apparatus used to perform measurements and calculations. However, particularly in the case where the device 10, 110 is a passive one that does not actively transmit the measurement data, the pump 510 may alternatively perform milk expression volume calculations and transmit this data to the external computer. Examples of breast pumps 510 that may be integrated into the system include those breast pumps that are disclosed in provisional application Ser. No. 62/027,685, titled "Breast Pump System and Methods", filed Jul. 22, 2014, which is hereby incorporated herein, by reference thereto. Breast pump 510 includes at least one sensor 54 and circuitry 22' configured to process signals form the at least one sensor 54 to calculate estimates of milk volume expressed. By providing breast pump 510 with an antenna 28, the circuitry 22' including a transmitter can transmit the milk volume expression data to the external computer(s)/server 70 to be integrated with the data received from device 10/110.

Further optionally, data from both device 10/110 and breast pump 510 (or other disclosed devices) can be received by the external computer to validate one set of data against the other and/or calculate some type of average of the two data sets received.

Figure 28:
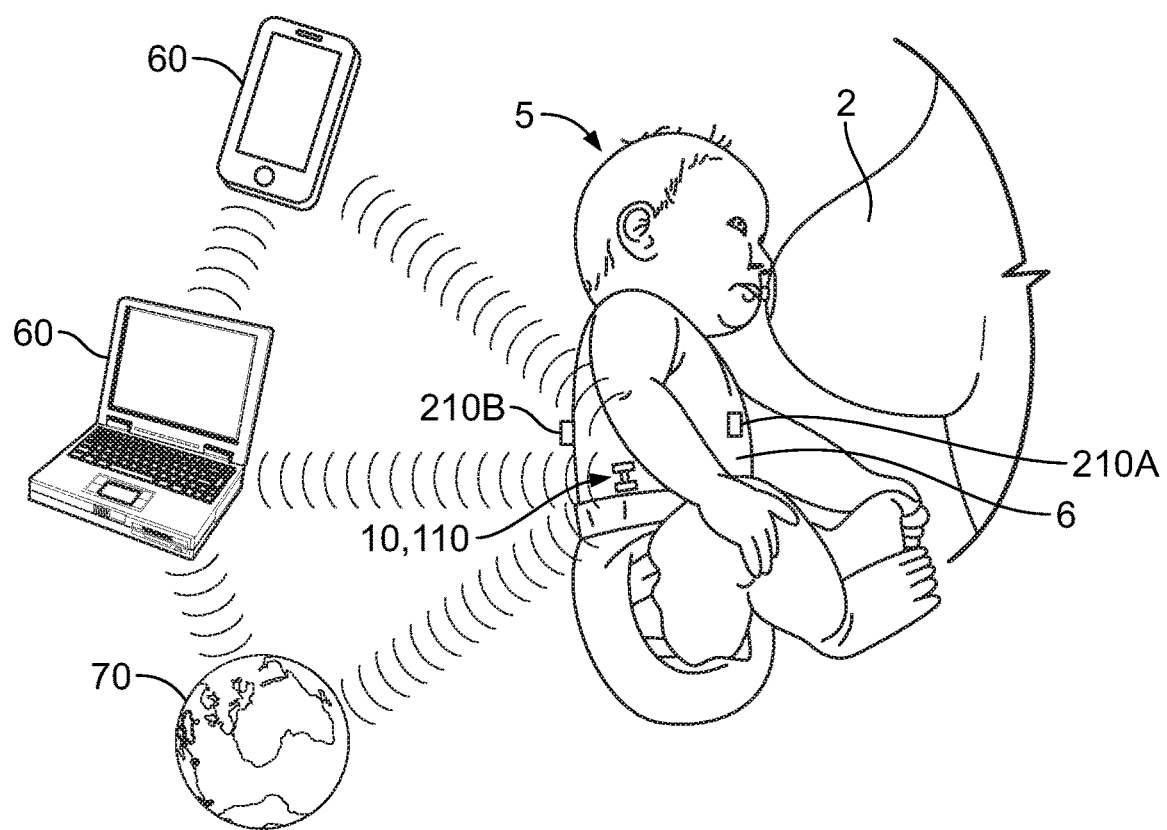
FIG. 28 illustrates a device having been adhered to the skin overlying the stomach of a feeding baby, according to an embodiment of the present disclosure.

FIG. 28 illustrates a device 10 or 110 having been adhered to the skin overlying the stomach 6 of a feeding baby 5. The device 10 can be active and transmit changes regarding the stretching of the skin in the same manner as the breast embodiments. Alternatively, a passive device, such as 110 can be used and can be photographed pre- and post-feeding using the smartphone 60 to input the data used to calculate the volume in the baby's stomach. Alternatively to the devices 10, 110 that measure physical changes in the dimensions of the skin, a device 210 may be attached to the skin over the stomach to measure impedance. In this embodiment, a lead 210A is attached over the stomach 6 and a probe 210B is attached on the back, opposite the lead 210A, or vice versa. Similar to calculation of changes in breast volume by measuring impedance, as described above, changes in impedance through and/or around the baby's stomach can be correlated with volume contained by the stomach. Sensors/electrodes 201A, 210B are placed on the torso to determine impedance changes after a slight current is applied.

Figure 32:
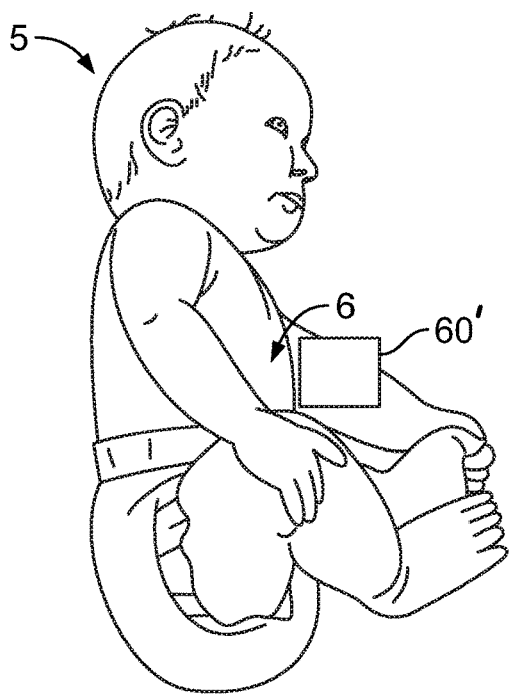
FIG. 32 illustrates a device placed against the stomach of a baby before feeding, to take a baseline measurement, according to an embodiment of the present disclosure.

Further alternatively, acoustic assessment of the volume in the stomach 6 may be may be performed. An external computing device 60', preferably, but not necessarily, a small handheld device is configured to emit and receive an acoustic wave, e.g., a portable ultrasound device, a smart phone or other computer configured with an ultrasound transducer and operating software, or other external computing device 60' configured to emit and receive acoustic waves. The device 60' may also be configured to process the received waves, or only to transduce the received waves to signals which are outputted to device 60, 70 for processing. The device 60' is placed against the stomach 6 before feeding and a baseline measure can be taken, e.g., see FIG. 32. After feeding, the user places the device 60' in the same or similar location and takes another reading. The device 60' emits a tone or spectrum of tones (which are not necessarily in the audible range). The reflected signal is characteristics and correlates with a change in fluid volume and hence the volume of milk ingested. It may also be able to characterize the amount of air ingested.

Figure 29:
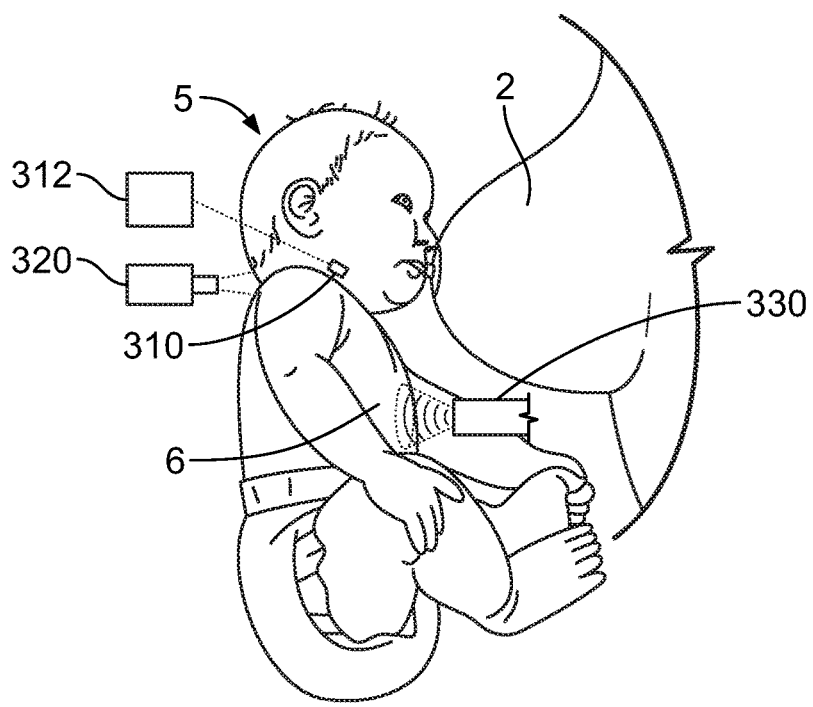
FIG. 29 illustrates an ultrasound machine being used to apply ultrasound to the stomach of an infant, with the echoes being received changing as a dependent function of volume in the stomach, according to an embodiment of the present disclosure.

FIG. 29 illustrates methods of estimating the volume of milk consumed by a baby 5 during a breastfeeding session. In one embodiment, a microphone 310 is adhered to or placed against the throat of the baby 5 and swallow sounds are recorded. By differentiating between the sounds that vary for a swallow full of milk and a swallow empty of milk, as well as swallows having intermediate amounts somewhere in between full and empty, a model can be made to correlate the swallow sound signature with the volume of milk contained in that swallow. Additionally, a camera can optionally be provided to view the throat as the baby 5 swallows, as an aid to counting the number of swallows during the feeding session. Otherwise the number of swallows can be audibly determined using the microphone 310 (and associated amplifier and recording equipment 312, types of which are known in the art). An ultrasound machine 330 can be used to apply ultrasound to the stomach, with the echoes being received changing as a dependent function of volume in the stomach.

In at least one embodiment, the echoes may be processed to average the signal, e.g., black/anechoic regions and echoic regions that corresponds with a change in volume. Ultrasonic imaging can be used to differentiate the stomach outline from its contents. By scanning, a three-dimensional image of the volume of the contents can also be created, which may be a more accurate estimate of volume compared to estimating based upon one or more two-dimensional images.

Acoustic sensing is configured to differentiate the signal characteristic of swallowing when the baby's mouth is full, or contains a significant amount of milk, versus when the baby' mouth is substantially empty and the baby is swallowing mostly air, to provide a more accurate estimate of the volume of milk consumed. Calibration can be performed by taking a calibration measurement while feeding the baby via a bottle. The bottle volume is entered and correlates with the signal, and these correlating data can be stored in the device to allow accurate measurements during breastfeeding.

FIG. 31 illustrates an embodiment in which an acoustic sensor 320 is attached to the breast 2 to be used for estimating volume of the breast 2. In this embodiment, acoustic sensor 320 is configured to emit a "ping", i.e., a sound wave into the breast and then receive echo signals from the same which can be used to calculate breast volume. That echo signal characteristics can define/correlate with a baseline and change in volume. A single sensor 320 may be used as the sound wave emitter/receiver for both emitting the signal and receiving echo signals that can be either analyzed with a computer processor on board the sensor 320, but more preferably outputted to an external computer 60, 70 for processing. Alternatively, the system may employ two sensors 320 and 320" (shown in phantom in FIG. 31) wherein sensor 320 emits the signal and sensor 320' receives the signals that pass through the breast. In this alternative embodiment, the sensors 320, 320' could alternatively or additionally be used to measure impedance and impedance changes in the breast 2, which can be correlated to changes in breast volume.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure as described herein.

That which is claimed is:

1. A method of assessing milk volume expressed from a breast, the method comprising:
   associating a measurement device with the breast, the measurement device includes a plurality of markers configured to be placed on the breast and being formed on a material that is configured to conform to a curvature of the breast, wherein each of the plurality of markers have a different pattern;
   calculating a change in breast volume using the measurement device by taking circumferential and longitudinal measurements of the breast using the plurality of markers of the measurement device; and
   assessing milk volume expressed from the breast using the change in breast volume.

2. The method of claim 1, further comprising taking a circumferential measurement of the breast.

3. The method of claim 1, further comprising taking an anterior posterior measurement of the breast.

4. The method of claim 1, further comprising assessing a change in distance between the plurality of markers.

5. The method of claim 1, further comprising providing a controller configured to wirelessly communicate with the measurement device.

6. The method of claim 1, wherein the measurement device automatically communicates information with an external device.

7. The method of claim 1, wherein the measurement device automatically communicates information to an internet server.

8. The method of claim 1, wherein the measurement device communicates with a smartphone.

9. The method of claim 1, wherein the measurement device includes an antenna.

10. The method of claim 1, wherein calculating the change in breast volume is accomplished visually by an imaging visual device.

11. The method of claim 1, further comprising measuring distances between the plurality of markers.

12. The method of claim 1, further comprising taking initial measurements of a distance between the plurality of markers, wherein the initial measurements are taken when the breast is in one of a pre-breast feeding, post-breast feeding, pre-pumping, or post-pumping state.

13. The method of claim 1, further comprising taking measurements of distances between the plurality of markers prior to and after feeding from the breast by a child.

14. The method of claim 1, further comprising tracking the change in the breast volume.

\* \* \* \* \*